US010551738B2

(12) United States Patent
Park et al.

(10) Patent No.: US 10,551,738 B2
(45) Date of Patent: *Feb. 4, 2020

(54) PHOTORESIST COMPOSITIONS, INTERMEDIATE PRODUCTS, AND METHODS OF MANUFACTURING PATTERNED DEVICES AND SEMICONDUCTOR DEVICES

(71) Applicant: SAMSUNG ELECTRONICS CO., LTD., Suwon-si, Gyeonggi-do (KR)

(72) Inventors: Jin Park, Yongin-si (KR); Hyun-Woo Kim, Seongnam-si (KR); Jin-Kyu Han, Seongnam-si (KR)

(73) Assignee: Samsung Electronics Co., Ltd., Suwon-si, Gyeonggi-do (KR)

(*) Notice: Subject to any disclaimer, the term of this patent is extended or adjusted under 35 U.S.C. 154(b) by 0 days.

This patent is subject to a terminal disclaimer.

(21) Appl. No.: 16/256,827

(22) Filed: Jan. 24, 2019

(65) Prior Publication Data
US 2019/0179227 A1 Jun. 13, 2019

Related U.S. Application Data

(63) Continuation of application No. 15/372,773, filed on Dec. 8, 2016, now Pat. No. 10,234,760.

(30) Foreign Application Priority Data

Dec. 9, 2015 (KR) ........................ 10-2015-0175067

(51) Int. Cl.
G03F 7/004 (2006.01)
G03F 7/039 (2006.01)
G03F 7/075 (2006.01)
H01L 21/027 (2006.01)
C08G 77/48 (2006.01)
C07C 381/12 (2006.01)
H01L 29/66 (2006.01)
H01L 21/311 (2006.01)
H01L 21/768 (2006.01)
H01L 21/3213 (2006.01)
H01L 29/51 (2006.01)

(52) U.S. Cl.
CPC .......... G03F 7/0046 (2013.01); C07C 381/12 (2013.01); C08G 77/48 (2013.01); G03F 7/0045 (2013.01); G03F 7/0392 (2013.01); G03F 7/0751 (2013.01); G03F 7/0758 (2013.01); H01L 21/0273 (2013.01); H01L 21/31144 (2013.01); H01L 21/32139 (2013.01); H01L 21/7684 (2013.01); H01L 21/76802 (2013.01); H01L 21/76843 (2013.01); H01L 21/76877 (2013.01); H01L 29/6545 (2013.01); H01L 29/66636 (2013.01); H01L 29/66795 (2013.01); H01L 29/513 (2013.01); H01L 29/518 (2013.01); H01L 29/665 (2013.01)

(58) Field of Classification Search
CPC .... G03F 7/0046; G03F 7/0045; G03F 7/0392; G03F 7/0751; G03F 7/0758; C07C 381/12; H01L 21/0273; H01L 21/31144; H01L 21/32139; H01L 21/7684; H01L 21/76802; H01L 21/76843; H01L 21/76877; H01L 29/66545; H01L 29/66636; H01L 29/66795
See application file for complete search history.

(56) References Cited

U.S. PATENT DOCUMENTS

| 3,418,289 A | 12/1968 | Hogsed |
| 3,998,856 A | 12/1976 | Rosenberger |
| 4,599,393 A | 7/1986 | Policastro |
| 4,975,222 A | 12/1990 | Yoshino et al. |
| 5,187,244 A | 2/1993 | Sugimori |
| 5,254,664 A | 10/1993 | Narang |
| 5,856,071 A | 1/1999 | Kotachi |
| 5,885,745 A | 3/1999 | Marrocco |
| 6,444,408 B1* | 9/2002 | Brock ................... G03F 7/0045 430/270.1 |
| 6,797,449 B2 | 9/2004 | Nakamura |
| 6,991,888 B2 | 1/2006 | Padmanaban et al. |
| 7,326,518 B2 | 2/2008 | Cameron et al. |
| 7,425,404 B2 | 9/2008 | Tarutani |
| 7,678,528 B2 | 3/2010 | Rahman et al. |
| 8,652,752 B2 | 2/2014 | Hayoz et al. |
| 8,846,295 B2 | 9/2014 | Chen et al. |
| 8,932,793 B2 | 1/2015 | Cameron |
| 8,999,625 B2 | 4/2015 | Glodde et al. |

(Continued)

FOREIGN PATENT DOCUMENTS

| JP | 2010208023 A | 9/2010 |
| KR | 100241492 B1 | 11/1999 |

(Continued)

OTHER PUBLICATIONS

Bulgokova et al., "Methacrylic silicon-containing tercopolymers for chemically amplified resists", Poly. Sci. Ser. B. vol. 52(5-6) pp. 353-361 (2010).
Ober et al., "Block copolymers as lithographic materials", J. Photopoly. Sci. Tech., vol. 9(1) pp. 1-12 (1996).
Bonfils et al., "Influence du vieillssement d'une solution renferman in polystyrene silicie . . . ", Makromol. Chem., vol. 193 pp. 143-156 (1992).

Primary Examiner — Martin J Angebranndt
(74) Attorney, Agent, or Firm — Volentine, Whitt & Francos, PLLC

(57) ABSTRACT

A photoresist composition includes a photoresist polymer including a repeating unit to which a silicon-containing leaving group is combined, a photo-fluorine generator including a sulfonium fluoride, and a solvent.

13 Claims, 27 Drawing Sheets

(56) References Cited

U.S. PATENT DOCUMENTS

| | | |
|---|---|---|
| 9,029,065 B2 | 5/2015 | Aqad et al. |
| 9,045,398 B2 | 6/2015 | Suzuki et al. |
| 10,234,760 B2 * | 3/2019 | Park .................... G03F 7/0045 |
| 2002/0182535 A1 | 12/2002 | Maeda et al. |
| 2003/0003762 A1 | 1/2003 | Cotte |
| 2004/0131973 A1 | 7/2004 | Tao |
| 2004/0175644 A1 | 9/2004 | Abdourazak et al. |
| 2005/0143270 A1 | 6/2005 | Wojtczak |
| 2006/0046161 A1 | 3/2006 | Yin |
| 2007/0287766 A1 | 12/2007 | Kucynski |
| 2009/0107520 A1 | 4/2009 | Lee |
| 2011/0118165 A1 | 5/2011 | Lee |
| 2012/0130117 A1 | 5/2012 | Makabe et al. |
| 2015/0037735 A1 | 2/2015 | Yang et al. |
| 2015/0044509 A1 | 2/2015 | Kunimoto et al. |
| 2015/0118188 A1 | 4/2015 | Weitekamp et al. |
| 2015/0246875 A1 | 9/2015 | Friedrich et al. |

FOREIGN PATENT DOCUMENTS

| | | |
|---|---|---|
| KR | 1020020080736 A | 10/2002 |
| KR | 1020020080737 A | 10/2002 |
| KR | 1020030028103 A | 4/2003 |
| WO | 2008044741 A | 4/2008 |

\* cited by examiner

PHOTORESIST COMPOSITIONS, INTERMEDIATE PRODUCTS, AND METHODS OF MANUFACTURING PATTERNED DEVICES AND SEMICONDUCTOR DEVICES

CROSS-REFERENCE TO RELATED APPLICATION

This a Continuation of U.S. application Ser. No. 15/372,773, filed Dec. 8, 2015, in which a claim of priority under 35 USC § 119 is made to Korean Patent Application No. 10-2015-0175067, filed on Dec. 9, 2015, in the Korean Intellectual Property Office (KIPO), the content of which is incorporated by reference herein in its entirety.

BACKGROUND

Example embodiments relate to photoresist compositions, intermediate products having photoresistive layers, and to methods of manufacturing patterned devices and semiconductor devices. More particularly, example embodiments relate to photoresist compositions including a photosensitive polymer, to intermediate products having photoresistive layers including a photoresistive polymer, and to methods of manufacturing patterned devices and semiconductor devices using photoresist compositions including a photosensitive polymer.

Photolithography processes are utilized to form material layer patterns in semiconductor devices. In one type of photolithography process, a photoresist layer is partially exposed in an exposure process (e.g., by a light source) to define an exposed portion and a non-exposed portion of the photoresist layer, and then either the exposed portion or the non-exposed portion is removed in a developing process to form a photoresist pattern. An object layer underlying the photoresist pattern may be etched using the photoresist pattern as an etching mask to form a desired pattern in the object layer.

SUMMARY

According to an aspect of the inventive concepts, there is provided a photoresist composition that includes a photoresist polymer including a repeating unit to which a silicon-containing leaving group is combined, a photo-fluorine generator including a sulfonium fluoride, and a solvent.

According to another aspect of the inventive concepts, there is provided a photoresist composition that includes a photoresist polymer including a repeating unit to which a silicon-containing leaving group is combined, a photo-fluorine generator, a sensitizer capable of generating fluorine, and a solvent.

According to still another aspect of the inventive concepts, there is provided a method of manufacturing a patterned device. In the method, an object layer is formed on a substrate. A photoresist layer is formed on the object layer by coating the object layer with a photoresist composition. The photoresist composition includes a photoresist polymer including a repeating unit to which a silicon-containing leaving group is combined, a photo-fluorine generator including a sulfonium fluoride and a solvent. An exposure process is performed on the photoresist layer such that the photoresist layer may be divided into an exposed portion and a non-exposed portion. The exposed portion is removed to form a photoresist pattern. The object layer is patterned using the photoresist pattern.

According to yet another aspect of the inventive concepts, there is provided a method of manufacturing a semiconductor device. In the method, an isolation layer is formed on a substrate to define active patterns on the substrate. A gate structure is formed on the isolation layer and the active patterns. Contacts electrically connected to the active patterns are formed. An insulating interlayer covering the gate structure and the contacts is formed. A photoresist layer is formed on the insulating interlayer by coating the insulating layer with a photoresist composition. The photoresist composition includes a photoresist polymer including a repeating unit to which a silicon-containing leaving group is combined, a photo-fluorine generator including a sulfonium fluoride, and a solvent. The photoresist layer is partially removed to form a photoresist pattern. The insulating interlayer is partially etched using the photoresist pattern as a mask to form openings through which the contacts are exposed. Wirings are formed in the openings to be electrically connected to the contacts.

According to another aspect of the inventive concepts, an intermediate product is provided which includes a semiconductor substrate, an object layer on the semiconductor layer, and a photoresistive layer on the object layer. The photoresistive layer includes a photoresistive compound, and the photoresistive compound includes a photoresist polymer including a repeating unit to which a silicon-containing leaving group is combined, a photo-fluorine generator including a sulfonium fluoride, and a solvent.

BRIEF DESCRIPTION OF THE DRAWINGS

The above and other aspects of the inventive concepts will become readily apparent from the detailed description that follows taken in conjunction with the accompanying drawings which represent non-limiting, example embodiments as described herein.

DESCRIPTION OF EMBODIMENTS

Figure 1:
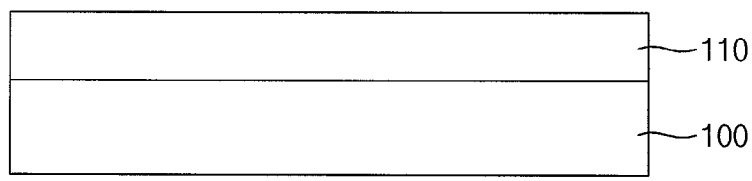
FIGS. 1 to 6 are cross-sectional views for reference in describing a method of forming a pattern in accordance with example embodiments.

Various example embodiments will be described more fully hereinafter with reference to the accompanying drawings, in which some example embodiments are shown. The present inventive concept may, however, be embodied in many different forms and should not be construed as limited to the example embodiments set forth herein. Rather, these example embodiments are provided so that this description will be thorough and complete, and will fully convey the scope of the present inventive concept to those skilled in the art. In the drawings, the sizes and relative sizes of layers and regions may be exaggerated for clarity.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numerals refer to like elements throughout. As used herein, the term "and/or" includes any and all combinations of one or more of the associated listed items.

It will be understood that, although the terms first, second, third, fourth etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present inventive concept.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular example embodiments only and is not intended to be limiting of the present inventive concept. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized example embodiments (and intermediate structures). As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the present inventive concept.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Although corresponding plan views and/or perspective views of some cross-sectional view(s) may not be shown, the cross-sectional view(s) of device structures illustrated herein provide support for a plurality of device structures that extend along two different directions as would be illustrated in a plan view, and/or in three different directions as would be illustrated in a perspective view. The two different directions may or may not be orthogonal to each other. The three different directions may include a third direction that may be orthogonal to the two different directions. The plurality of device structures may be integrated in a same electronic device. For example, when a device structure (e.g., a memory cell structure or a transistor structure) is illustrated in a cross-sectional view, an electronic device may include a plurality of the device structures (e.g., memory cell structures or transistor structures), as would be illustrated by a plan view of the electronic device. The plurality of device structures may be arranged in an array and/or in a two-dimensional pattern.

A photoresist composition in accordance with example embodiments may be utilized in a photo-lithography process for forming, for example, an insulation pattern, a gate electrode and/or a wiring structure included in a semiconductor device. In some example embodiments, the photoresist composition may exhibit sensitivity to an extreme ultraviolet (EUV) light source.

In example embodiments, the photoresist composition includes a photoresist polymer, a photo-fluorine generator and a solvent. In some other example embodiments, the photoresist composition further includes a sensitizer.

A fluorine-ion ($F^-$) may be generated through a reaction between the photo-fluorine generator and a photon created from, for example, the EUV light source.

In example embodiments, the photo-fluorine generator includes a sulfonium fluoride in which a sulfonium ion and the fluorine ion as a counter ion may be combined.

For example, a structure of the photo-fluorine generator may be represented by the following Chemical Formula 1.

Chemical Formula 1

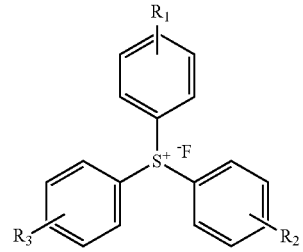

In the Chemical Formula 1 above, $R_1$, $R_2$ and $R_3$ may be independently hydrogen, a C1-C20 aliphatic hydrocarbon group, or a C1-C20 hetero aliphatic hydrocarbon group including at least one of nitrogen (N), oxygen (O) or halogen. Here and throughout this disclosure, the term "independently" means that the selection of one element or constituent is not dependent upon the selection of the other elements or constituents. Accordingly, none, some or all of the listed elements or constituents may be the same as each other. For example, the case of Chemical Formula 1, all of $R_1$, $R_2$ and $R_3$ can be the same as each other, two of $R_1$, $R_2$ and $R_3$ can be the same as each other, or none of $R_1$, $R_2$ and $R_3$ can be the same as each other.

In the sulfonium ion, a rearrangement reaction may occur in at least one of phenyl rings combined to sulfur (S) through a photo-chemical reaction with a photon. A proton (H+) may be generated from the sulfonium ion by an electron transfer derived from the rearrangement reaction. The proton may be combined with the fluorine ion to create fluoric acid (HF).

As described above, the sulfonium ion may be stabilized by the rearrangement reaction, so that a generation of the fluorine ion or HF may be facilitated even by a relatively small quantity of photons.

In example embodiments, the photoresist polymer may include a repeating unit that may be combined to a back-bone chain and may include a silicon-containing leaving group.

The back-bone chain may include a carbon chain included in a photoresist material. For example, the back-bone chain may include a polymer chain such as novolak, polystyrene, polyhydroxystyrene (PHS), polyacrylate, polymethacrylate, polyvinyl ester, polyvinyl ether, polyolefin, polynorbornene, polyester, polyamide, polycarbonate or the like. In example embodiments, novolak, polystyrene, PHS or polyacrylate are used as the back-bone chain.

The silicon-containing leaving group may include, for example, a silyl group. For example, the silicon-containing leaving group may include trimethyl silyl (TMS), tert-butyl dimethyl silyl (TBDMS), triisopropyl silyl (TIPS), tert-butyl diphenyl silyl (TBDPS) or a combination thereof.

The silicon-containing leaving group may be combined to the back-bone chain via a linker group. In some embodiments, the linker group may include an ester group.

For example, a structure of the repeating unit including the silicon-containing leaving group may be represented by the following Chemical Formula 2 or Chemical Formula 3.

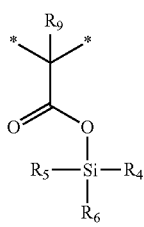

Chemical Formula 2

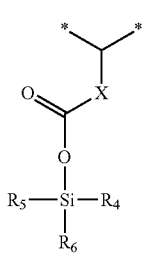

Chemical Formula 3

In the Chemical Formulae 2 and 3 above, $R_4$, $R_5$ and $R_6$ may be independently hydrogen, a C1-C20 alkyl group, a C3-C20 cycloalkyl group or a C6-C30 aromatic group. $R_4$, $R_5$ and $R_6$ may be the same as or different from each other. X of Chemical Formula 3 may represent a divalent group selected from styrene, hydroxystyrene, acrylate, benzene, hydroxybenzene, C1-C6 alkylene, C6-C30 arylene, carbonyl, oxy, a C2-C30 unsaturated aliphatic group or a combination thereof. Consistent with the definition of "independently" previously set forth, two or more of $R_4$, $R_5$ and $R_6$ may be the same as each other, or $R_4$, $R_5$ and $R_6$ may all be different from each other. $R_9$ may be hydrogen or methyl group.

In example embodiments, a fluorine ion (F−) may be generated from HF formed by the photo-fluorine generator. The fluorine ion may attack a silicon atom of the repeating unit that may include the silicon-containing leaving group so that the silicon-containing leaving group may be separated or deprotected from the repeating unit. A proton (H+) generated from HF may be trapped at a site from which the silicon-containing group may be separated to create a hydroxyl group or a carboxyl group. Thus, an exposed portion of the photoresist polymer may have increased hydrophilicity and/or polarity.

In some example embodiments, the silicon-containing leaving group is combined with at least two linker groups. For example, the silicon-containing leaving group may be connected to two ester groups.

In this case, a structure of the repeating unit including the silicon-containing leaving group may be represented by the following Chemical Formula 4.

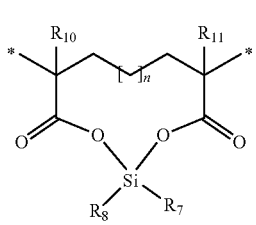

Chemical Formula 4

In the Chemical Formula 4 above, $R_7$ and $R_8$ may be independently hydrogen, a C1-C20 alkyl group, a C3-C20 cycloalkyl group or a C6-C30 aromatic group, and n may represent a natural number of 1 to 20. $R_{10}$ and $R_{11}$ may be independently hydrogen or methyl group. Consistent with the definition of "independently" previously set forth, $R_7$ and $R_8$ may be the same as or different from each other.

As described above, the fluorine ion generated from the photo-fluorine generator may attack a silicon atom of the repeating unit represented by Chemical Formula 4 to create two hydroxyl groups or carboxylic groups. Thus, hydrophilicity and/or polarity of the exposed portion may be further increased.

The sensitizer may be added to amplify the number of the fluorine ions by photons introduced from the light source.

In example embodiments, the sensitizer includes an aromatic compound including a fluorine substituent. In some other example embodiments, the sensitizer further includes a substituent containing an unshared electron pair.

In some example embodiments, the structure of the sensitizer is represented by the following Chemical Formula 5.

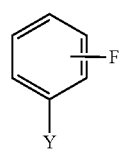

Chemical Formula 5

In the Chemical Formula 5 above, F represents the fluorine substituent. The number of the fluorine substituents may be an integer between 1 and 5 both inclusive. Y represents the substituent containing the unshared electron pair, and may include a hydroxyl group, an alkoxy group, a thiol group or an amino group.

In some embodiments, the sensitizer may be represented by the following Chemical Formula 6.

Chemical Formula 6

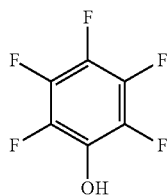

When the sensitizer is exposed to the photons from the light source, for example, resonance stabilization structures may be formed by the unshared electron pair included in the hydroxyl group and a benzene ring. A secondary electron may be created by the resonance stabilization to release a fluorine ion.

In some example embodiments, a plurality of the fluorine ions are released from one molecular of the sensitizer. Therefore, sensitivity in a photo-lithography process utilizing the photoresist composition may be further enhanced.

In some example embodiments, the sensitizer is coupled to the back-bone chain of the photoresist polymer as a sensitizer repeating unit. The sensitizer repeating unit may include one to four fluorine substituents. For example, the sensitizer repeating unit may be represented by the following Chemical Formula 7.

Chemical Formula 7

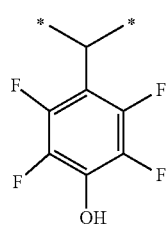

The solvent may include an organic solvent exhibiting favorable solubility for a polymer material, and a favorable coatability (e.g., good coating characteristics) for formation of a uniform photoresist layer. Nonlimiting examples of the solvent include cyclohexanone, cyclopentanone, tetrahydrofuran (THF), dimethylformamide, propylene glycol monomethyl ether acetate (PGMEA), ethyl lactate, methyl ethyl ketone, benzene or toluene. These may be used alone or in a combination of two or more thereof.

The photoresist composition may further include an additive for improving chemical and physical properties of a photoresist layer formed from the photoresist composition. The additive may include, for example, a surfactant, a leveling agent, a viscosity modifier, and so on.

In example embodiments, the photoresist composition includes the photoresist polymer in a range from about 5 weight percent (wt %) to about 20 wt %, the photo-fluorine generator in a range from about 0.1 wt % to about 5 wt %, the sensitizer in a range from about 0.01 wt % to about 1 wt %, the additive in a range from about 0.01 wt % to about 1 wt %, and the solvent in a range from about 75 wt % to about 94 wt %, based on a total weight of the composition. However, the inventive concepts are not limited to these composition ranges.

In example embodiments, the photoresist composition does not include a photo-acid generator (PAG). In this case, defects of a photoresist pattern caused by an irregular diffusion of an acid from the PAG may be substantially prevented or reduced.

The photoresist composition according to example embodiments may be referred to as a positive-type composition. For example, when the exposure process may be performed on the photoresist layer formed from the composition, an active fluorine such as a fluorine ion may be generated from the photo-fluorine generator at an exposed portion. The silicon-containing leaving group of the photoresist polymer may be removed by the active fluorine. A hydroxyl group or a carboxylic group may be created at a site from which the silicon-containing leaving group is removed. Thus, the exposed portion may have hydrophilicity and/or solubility greater than those of a non-exposed portion. Accordingly, the exposed portion may be selectively removed by an etching process or a developing process to form a photoresist pattern.

According to example embodiments as described above, a photoresist composition includes a photo-fluorine generator. The photo-fluorine generator may generate active fluorine such as the fluorine ion, rather than using a PAG to create acid in which mobility and diffusion are not easily controlled. Thus, a photoresist pattern having desired (or predetermined) line width and/or pitch may be formed from the photoresist composition. Further, the sulfonium fluoride may be used as the photo-fluorine generator to facilitate the generation of the active fluorine, and the sensitizer may be added to implement a photo-lithography system with a high sensitivity.

FIGS. 1 to 6 are cross-sectional views for reference in describing a method of manufacturing a patterned device in accordance with example embodiments. In the example of FIGS. 1 to 6, a patterned device is obtained utilizing the photoresist compositions of the previous example embodiments described above.

Referring to FIG. 1, an object layer 110 may be formed on a substrate 100. The substrate 100 may be a semiconductor substrate (such as a substrate completely formed of semiconductor material, or a semiconductor-on-insulator substrate). For example, the substrate 100 may include a silicon substrate, a germanium substrate, a silicon-germanium substrate, a silicon-on-insulator (SOI) substrate or a germanium-on-insulator (GOI) substrate. In example embodiments, the substrate 100 includes a group III-V compound such as GaP, GaAs or GaSb.

An image may be transferred from a photoresist pattern to the object layer 110 so that the object layer 110 may be converted to a desired (or predetermined) pattern. In some embodiments, the object layer 110 may be formed of an insulative material such as silicon oxide, silicon nitride or silicon oxynitride. In some embodiments, the object layer 110 may be formed of a conductive material such as a metal, a metal nitride, a metal silicide or a metal silicide nitride. In some embodiments, the object layer 110 may be formed of a semiconductor material such as polysilicon.

The object layer 110 may be formed by at least one deposition process. For example, the objection layer 110 may be formed using at least one of a chemical vapor deposition (CVD) process, a plasma enhanced chemical vapor deposition (PECVD) process, a low pressure chemical vapor deposition (LPCVD) process, a high density plasma chemical vapor deposition (HDP-CVD) process, a spin coating process, a sputtering process, an atomic layer deposition (ALD) process, or a physical vapor deposition (PVD) process.

Figure 2:
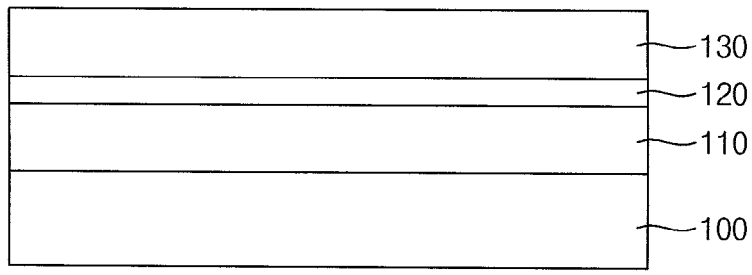

Referring to FIG. 2, a lower coating layer 120 and a photoresist layer 130 may be formed sequentially on the object layer 110.

The lower coating layer 120 may serve as an adhesive layer for improving an adhesion between the photoresist layer 130 and the object layer 110, or a planarization layer. In some embodiments, the lower coating layer 120 may be formed as an organic-based or inorganic-based anti-reflective layer. In some embodiments, the lower coating layer 120 is formed of a polymer which is substantially the same as or similar to the photoresist polymers as described above.

In some embodiments, the formation of the lower coating layer 120 is omitted.

The photoresist composition according to example embodiments as described above may be coated on the lower coating layer 120 by, for example, a spin coating process, and may be preliminarily cured by a soft-baking process to form the photoresist layer 130.

According to the example embodiments described above, the photoresist composition includes a photoresist polymer, a photo-fluorine generator and a solvent. In some other example embodiments, the photoresist composition further includes the sensitizer.

Figure 3:
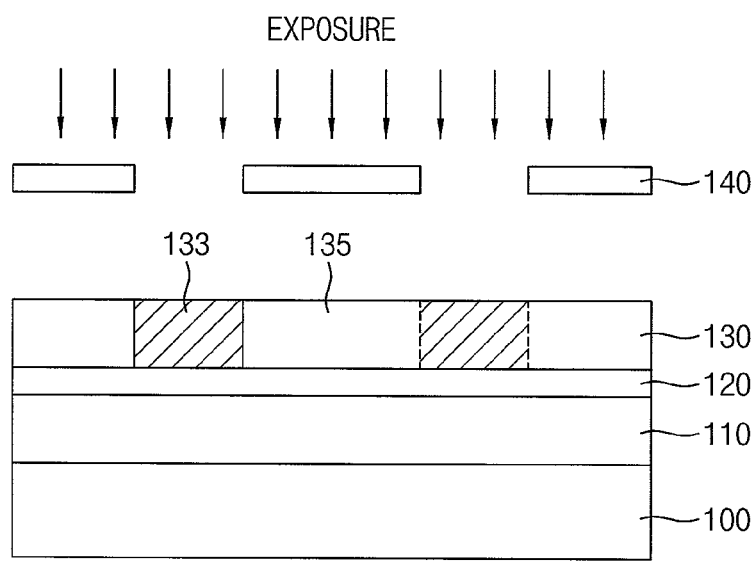

Referring to FIG. 3, an exposure process may be performed on the photoresist layer 130.

In example embodiments, an exposure mask 140 is placed on the photoresist layer 130, and a light may be irradiated through an opening or a transmission portion included in the exposure mask 140. Non-limiting examples of a light source used in the exposure process may include ArF, KrF, an electron beam, I-line or EUV. In example embodiments, an EUV light source is utilized in the exposure process.

The photoresist layer 130 may be divided into an exposed portion 133 and a non-exposed portion 135. In example embodiments, a chemical structure in the exposed portion 133 is modified through a Reaction Scheme mechanism described next. However, the inventive concepts are not limited by the reaction mechanism dividing the exposed portion 133 and the non-exposed portion 135.

For example, in the Reaction Scheme, the silicon-containing leaving group may be connected to the back-bone chain of the photoresist polymer via two ester groups as represented by Chemical Formula 4, and the sensitizer repeating unit may be also connected to the back-bone chain of the photoresist polymer as represented by Chemical Formula 7.

Reaction Scheme

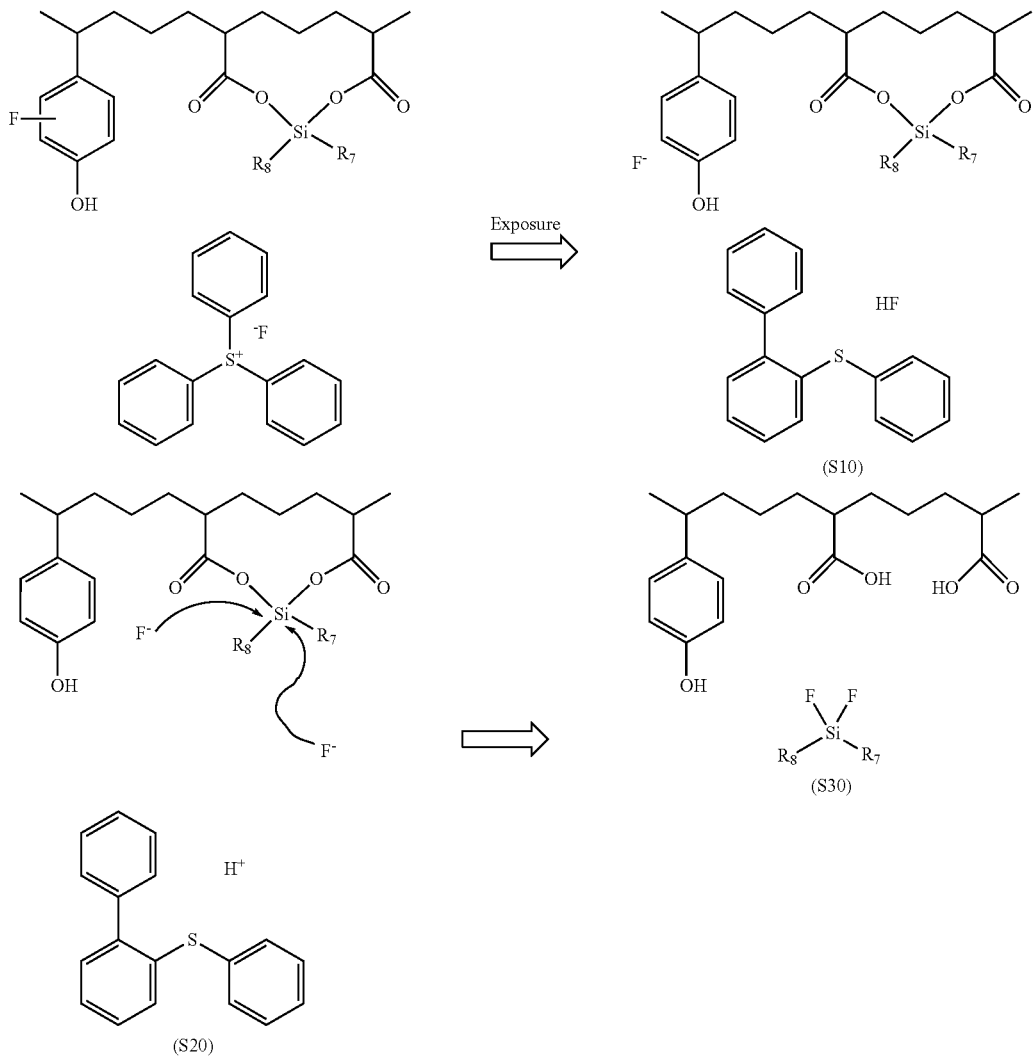

Referring to Reaction Scheme, when the exposure process may be performed using the EUV light source, in operation S10, a rearrangement of a phenyl ring may occur in the sulfonic fluoride serving as the photo-fluorine generator. Accordingly, one phenyl ring may substitute for hydrogen of another adjacent phenyl ring to create HF.

In the sensitizer repeating unit, a resonance stabilization may occur in a benzene ring and the unshared electron pair of a hydroxyl group by a photon introduced from the EUV light source to generate a secondary electron. Accordingly, at least one fluorine ion ($F^-$) may be generated from the sensitizer repeating unit.

In operation S20, a fluorine ion generated from HF and/or the fluorine ion generated from the sensitizer repeating unit may attack a silicon atom of the silicon-containing leaving group. For example, the silicon atom may be combined to two fluorine ions to be separated or deprotected from the photoresist polymer.

In operation S30, the ester group from which the silicon-containing group may be removed may accept a proton ($H^+$) from HF formed by the sulfonic fluoride so that a carboxylic acid may be formed. Thus, the exposed portion 133 may have the hydrophilicity and/or the polarity greater than those of the non-exposed portion 135.

As described with reference to the above Reaction Scheme, two carboxylic acids may be created by one silicon-containing leaving group, and thus the hydrophilicity and/or the polarity of the exposed portion 133 may be further increased.

The EUV light source may have a relatively small wavelength, and may be advantageous for forming a pattern of a fine pitch and a narrow line width. The exposure process may be performed by a reduced power using the EUV light source. However, as the power of the EUV light source becomes smaller, a quantity of photons may be also reduced to cause a reduction of a sensitivity in a photo-lithography process.

However, according to example embodiments as described above, an active fluorine such as the fluorine ion may be generated even by a relatively small quantity of photons due to the rearrangement reaction occurring in the photo-fluorine generator. The fluorine ions may be further created from the sensitizer or the sensitizer repeating unit through the resonance stabilization. Therefore, a photo-lithography process system having a high sensitivity may be realized. By not generating of an acid from a conventional PAG, a reduction of resolution and a pattern defect caused by an irregular mobility of the acid and/or a diffusion of the acid to the non-exposed portion 135 may be avoided.

Figure 4:
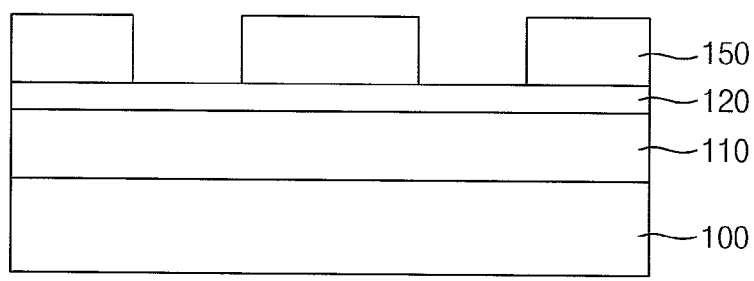

Referring to FIG. 4, the exposed portion 133 of the photoresist layer 130 may be selectively removed. Accordingly, a photoresist pattern 150 may be defined by the non-exposed portion 135 remaining on the object layer 110 or the lower coating layer 120.

In example embodiments, the exposed portion 133 are selectively removed using a developer solution such as an alcohol-based solution, or a hydroxide-based solution including, for example, tetra methyl ammonium hydroxide (TMAH).

As described with reference to the above Reaction Scheme, the exposed portion 133 may be converted to a pattern which may be significantly polar and/or hydrophilic relative to the non-exposed portion 135. Therefore, the exposed portion 133 may have a high solubility for the developer solution relatively to the non-exposed portion 135, and thus may be selectively removed by the developer solution such as TMAH.

In some embodiments, the exposed portion 133 may be removed by a dry etching process. The dry etching process may include a plasma etching process or a reactive ion etching (RIE) process using, for example, an oxygen gas.

The exposed portion 133, as described above, may include a highly hydrophilic and/or polar group such as carboxylic acid. Thus, the exposed portion 133 may have a relatively high affinity for the plasma etching process or the RIE process. Therefore, the exposed portion 133 may be selectively removed with a high etching selectivity relative to the non-exposed portion 135.

In some embodiments, a hard-baking process may be performed after removing the exposed portion 133 to form the photoresist pattern 150 from the non-exposed portion 135.

Figure 5:
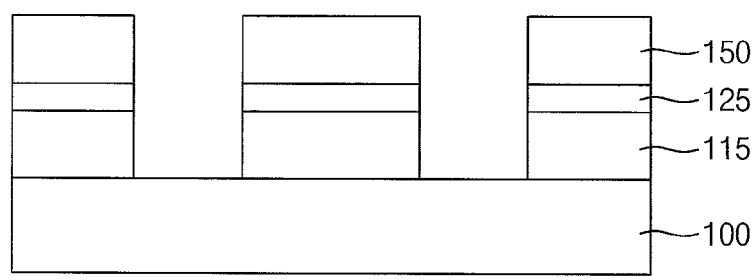

Referring to FIG. 5, the lower coating layer 120 and the object layer 110 may be etched using the photoresist pattern 150 as an etching mask. Accordingly, a lower coating pattern 125 and a target pattern 115 may be formed between the photoresist pattern 150 and the substrate 100.

The etching process may include a dry etching process and/or a wet etching process properly selected in consideration of an etching selectivity between the photoresist pattern 150 and the object layer 110.

In some embodiments, the dry etching process may include a plasma etching process.

In some embodiments, when performing the wet etching process, a proper etchant solution such as fluoric acid, phosphoric acid, sulfuric acid or peroxide may be selected depending on a material included in the object layer 110.

In some example embodiments, the lower coating layer 120 is removed during, for example, the developing process for removing the exposed portion 133 to form the lower coating pattern 125. For example, the fluorine ion created in the exposed portion 133 may be diffused to a portion of the lower coating layer 120 under the exposed portion 133. Accordingly, while removing the exposed portion 133, the portion of the lower coating layer 120 under the exposed portion 133 may be concurrently removed.

FIGS. 2 through 5 represent example embodiments of intermediate products in the course of manufacturing a patterned device. Here, the intermediate products include the substrate 100, the object layer 110, the lower coating layer 120, and the photoresist layer 130 (or 135 or 150). In some embodiments, however, the formation of the lower coating layer 120 is omitted as was mentioned previously.

Figure 6:
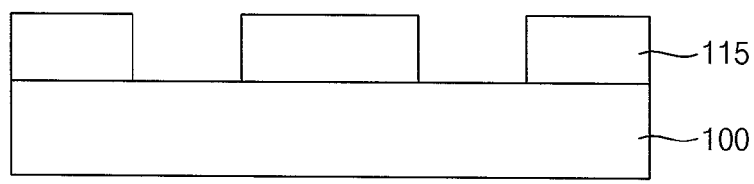

Referring to FIG. 6, the photoresist pattern 150 and the lower coating pattern 125 may be removed such that the target pattern 115 may remain on the substrate 100.

In example embodiments, the photoresist pattern 150 and the lower coating pattern 125 are removed by an ashing process and/or a strip process. In some other embodiments, the photoresist pattern 150 and the lower coating pattern 125 are removed by a planarization process, for example, a chemical mechanical polish (CMP) process.

If the object layer 110 includes a conductive material, the target pattern 115 may serve as a wiring, a contact, a pad, a plug, an interconnection structure, or the like of a semiconductor device.

If the object layer 110 includes an insulative material, the target pattern 115 may serve as a desired (or predetermined) insulation pattern, for example, an insulating interlayer pattern, a filling insulation pattern, or the like. In some embodiments, a portion of the object layer 110 removed by the above-mentioned photolithography process may be converted into a contact hole, an opening or a trench included in the insulation pattern.

FIGS. 7 to 13 cross-sectional views illustrating a method of forming a pattern in accordance with example embodiments.

For example, FIGS. 7 to 13 illustrate a method of forming a wiring structure utilizing the above-mentioned photoresist composition. Detailed descriptions on processes and/or materials substantially the same as or similar to those illustrated with reference to FIGS. 1 to 6 are omitted herein.

Figure 7:
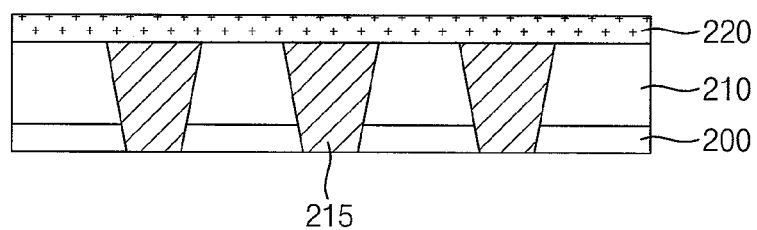
FIGS. 7 to 13 cross-sectional views for reference in describing a method of manufacturing a patterned device in accordance with example embodiments.

Referring to FIG. 7, a lower contact 215 extending through a lower insulation layer 210 may be formed. A plurality of the lower contacts 215 may be formed in the lower insulation layer 210.

In example embodiments, the lower insulation layer 210 is formed on a passivation layer 200, and a contact hole extending through the lower insulation layer 210 and the passivation layer 200 may be formed. The lower contact 215 may be formed by filling a conductive layer in the contact hole by a deposition process or a plating process.

In some embodiments, the method of forming the pattern in accordance with example embodiments as described with reference to FIGS. 1 to 6 may be implemented for the formation of the contact hole using the lower insulation layer 210 as an object layer.

The lower insulation layer 210 may be formed of an insulative material such as silicon oxide or silicon oxynitride. For example, the lower insulation layer 210 may be formed of a silicon oxide-based material such as plasma enhanced oxide (PEOX), tetraethyl orthosilicate (TEOS), silicate glass, or the like.

The passivation layer 200 may be formed of silicon nitride. The conductive layer may be formed of a metal such as aluminum (Al), tungsten (W) or copper (Cu), a metal nitride, a metal silicide and/or doped polysilicon.

In some embodiments, the lower contact 215 may be electrically connected to a circuit device or a lower wiring formed on a semiconductor substrate. Damages of the circuit device or the lower wiring while forming the contact hole may be limited and/or prevented by the passivation layer 200.

A first etch-stop layer 220 may be formed on the lower insulation layer 210 to cover the lower contacts 215. The first etch-stop layer 220 may be formed of silicon nitride or silicon oxynitride. For example, the first etch-stop layer 220 may be formed by, for example, a CVD process, a PECVD process, a sputtering process or an ALD process.

Figure 8:
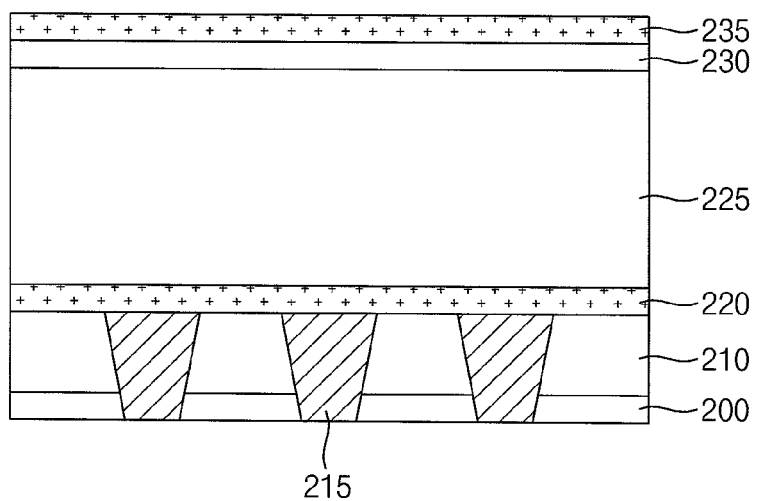

Referring to FIG. 8, an insulating interlayer 225, a buffer layer 230 and a second etch-stop layer 235 may be sequentially formed on the first etch-stop layer 220.

For example, the insulating interlayer 225 may be formed of the above-mentioned silicon oxide-based material, or a low dielectric (low-k) oxide such as polysiloxane or silsesquioxane. The buffer layer 230 and the second etch-stop layer 235 may be formed of, for example, silicon oxynitride and silicon nitride, respectively. A stress generated from the second etch-stop layer 235 may be alleviated or absorbed by the buffer layer 230.

The insulating interlayer 225, the buffer layer 230 and the second etch-stop layer 235 may be formed by a deposition process such as a CVD process, a PECVD process or a sputtering process such as an ion beam sputtering process, or a spin coating process, etc.

Figure 9:
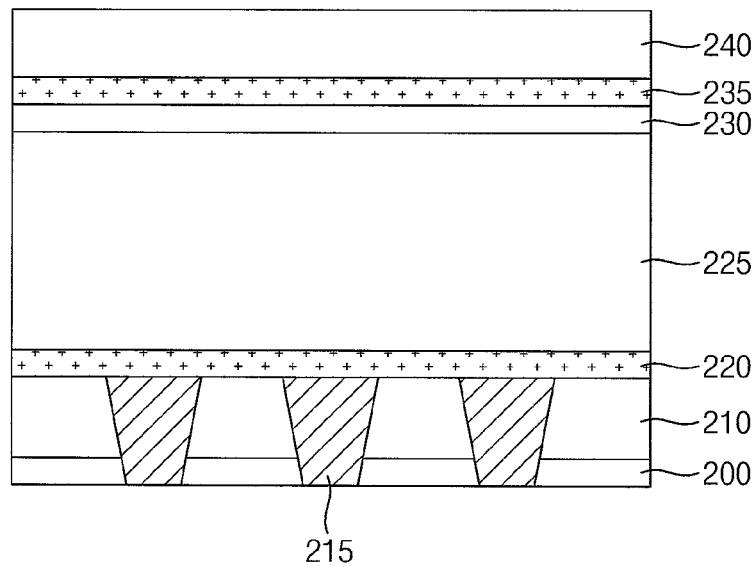

Referring to FIG. 9, a photoresist layer 240 may be formed on the second etch-stop layer 235.

The photoresist layer 240, as described in FIG. 2, may be formed using the photoresist composition according to example embodiments as described above. In some embodiments, a lower coating layer may be further formed before forming the photoresist layer 240.

The photoresist composition may include the photoresist polymer, the photo-fluorine generator and the solvent. In some example embodiments, the photoresist composition further includes the sensitizer.

The photo-fluorine generator may include the sulfonium fluoride as represented by, for example, the Chemical Formula 1 above. The photoresist polymer may include the repeating unit that may include the silicon-containing leaving group. The repeating unit may be represented by, for example, the Chemical Formula 2 or Chemical Formula 3 above. The silicon-containing leaving group may be combined to a back-bone chain of the photoresist polymer via at least two linker groups as represented by the Chemical Formula 4 above.

The sensitizer, as represented by the Chemical Formulae 5 and 6 above, may include an aromatic compound including a fluorine substituent and a substituent containing an unshared electron pair. In some example embodiments, the sensitizer is coupled to the photoresist polymer as a sensitizer repeating unit as represented by the Chemical Formula 7 above.

The photoresist composition may be coated to form a preliminary photoresist layer, and the preliminary photoresist layer may be thermally cured by, for example, a soft-baking process to form the photoresist layer 240.

Figure 10:
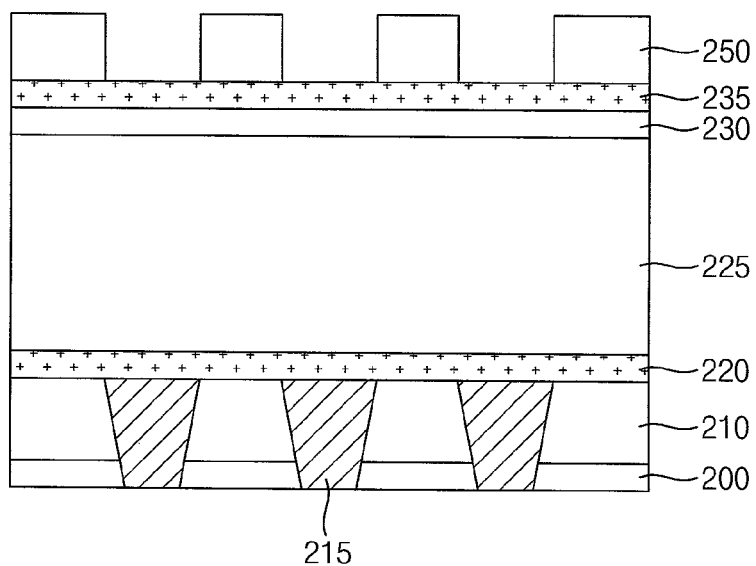

Referring to FIG. 10, processes substantially the same as or similar to those illustrated with reference to FIGS. 3 and 4 may be performed to form a photoresist pattern 250.

In example embodiments, an exposure process using, for example, an EUV light source is performed to generate an active fluorine such as a fluorine ion from the photo-fluorine generator included in an exposed portion. The fluorine ion may be transferred to the silicon-containing leaving group. Accordingly, a photo-chemical reaction may be induced by, for example, the above described Reaction Scheme, so that hydrophilicity and/or polarity of the exposed portion may be significantly increased relative to a non-exposed portion. Additionally, sensitivity in the exposed portion may be further enhanced by the sensitizer or the sensitizer repeating unit capable of releasing fluorine ions.

Subsequently, the exposed portion may be selectively removed by a developing process or a dry etching process such that the photoresist pattern 250 may be formed.

Figure 11:
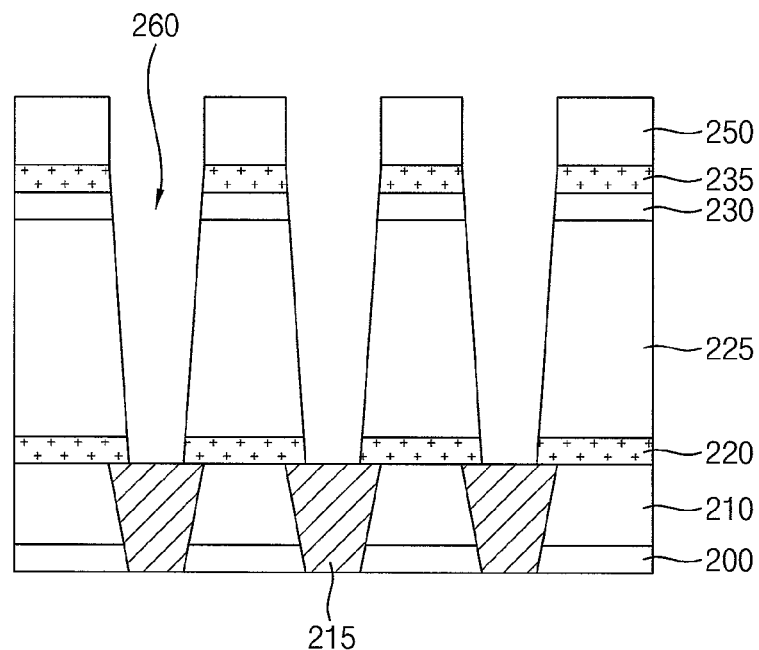

Referring to FIG. 11, the second etch-stop layer 235, the buffer layer 230, the insulating interlayer 225 and the first etch-stop layer 220 may be partially and sequentially etched using the photoresist pattern 250 as an etching mask. Thus, an opening 260 through which the lower contact 215 may be exposed may be formed.

The opening 260 may be formed by a dry etching process. The opening 260 may extend through the insulating interlayer 225 and the first etch-stop layer 220, and may at least partially expose an upper surface of the lower contact 215.

In some embodiments, the opening 260 may have a contact hole shape through which each lower contact 215 may be exposed. In some embodiments, the opening 260 may have a linear shape through which a plurality of the lower contacts 215 may be exposed.

Figure 12:
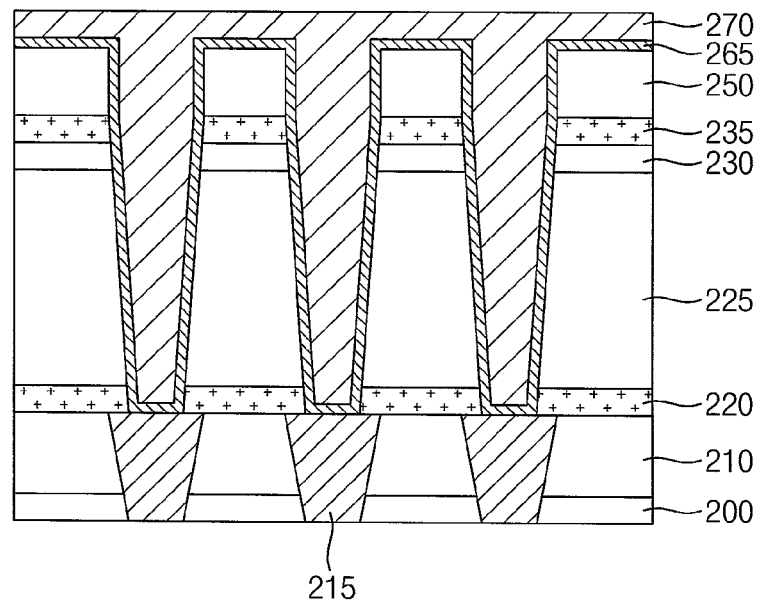

Referring to FIG. 12, a conductive layer 270 filling the openings 260 may be formed.

In example embodiments, a barrier layer 265 is formed conformally along top surfaces and sidewalls of the photoresist pattern 250, and sidewalls and bottoms of the openings 260 (or the exposed upper surfaces of the lower contacts 215). The conductive layer 270 may be formed on the barrier layer 265 to sufficiently fill the openings 260.

The barrier layer 265 may be formed of a metal nitride such as titanium nitride, tantalum nitride or tungsten nitride. The barrier layer 265 may limit and/or prevent a metal ingredient in the conductive layer 270 from being diffused into the insulating interlayer 225. The barrier layer 265 may also provide an adhesion for the formation of the conductive layer 270. The barrier layer 265 may be formed by, for example, a sputtering process or an ALD process.

The conductive layer 270 may be formed by, for example, an electroplating process. In this case, a seed layer may be formed conformally on the barrier layer 265 by a sputtering process using a copper target. A plating solution such as a copper sulfate solution may be used to induce an electrochemical reaction on the seed layer so that the conductive layer 270 including copper may be grown or precipitated on the seed layer.

In some embodiments, the conductive layer 270 may be deposited by a sputtering process using a metal target such as copper, tungsten or aluminum, or an ALD process.

Figure 13:
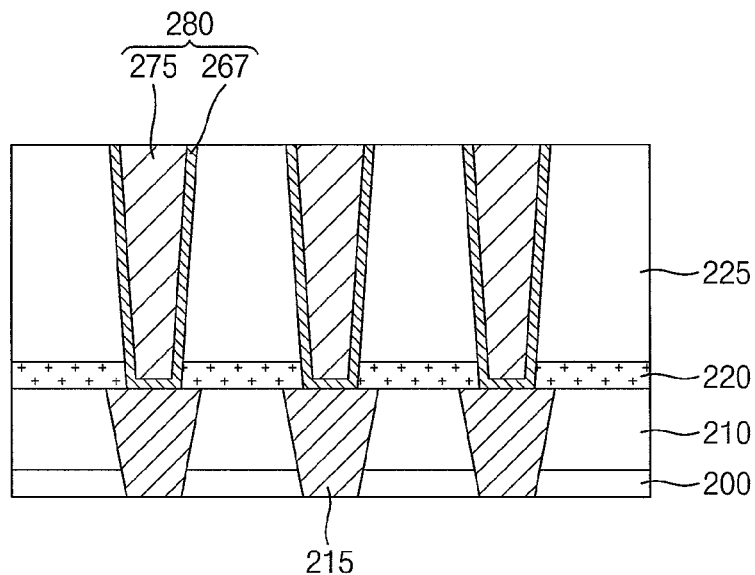

Referring to FIG. 13, upper portions of the conductive layer 270 and the barrier layer 265 may be planarized to form a conductive pattern 280.

In example embodiments, the upper portions of the conductive layer 270 and the barrier layer 265 are planarized by a CMP process until a top surface of the insulating interlayer 225 is exposed. The photoresist pattern 250, the second etch-stop layer 235 and the buffer layer 230 may be also removed by the planarization process.

Accordingly, the conductive pattern 280 electrically connected to the lower contact 215 may be formed in the opening 260. The conductive pattern 280 may include a barrier pattern 267 formed on the sidewall and the bottom of the opening 260, and a conductive filling pattern 275 filling a remaining portion of the opening 260 on the barrier pattern 267.

FIGS. 12 and 13 illustrate that the photoresist pattern 250 is removed by the planarization process for the formation of the conductive pattern 280. However, the photoresist pattern 250 may be removed after forming the opening 260 and before forming the barrier layer 265. For example, after forming the opening 260, the photoresist pattern 250 may be removed by an ashing process and/or a strip process.

In some embodiments, a wiring electrically connected to the conductive pattern 280 may be further formed on the insulating interlayer 225. For example, a metal layer may be formed on the insulating interlayer 225 and the conductive pattern 280. The metal layer may be patterned by a photolithography process utilizing the photoresist composition according to example embodiments as described above to form the wiring.

FIGS. 14 to 35 are top plan views and cross-sectional views illustrating a method of manufacturing a semiconductor device in accordance with example embodiments. For example, FIGS. 14 to 35 illustrate a method of manufacturing a logic semiconductor device. For example, the logic semiconductor device may include a fin field-effect transistor (FinFET).

Figure 14:
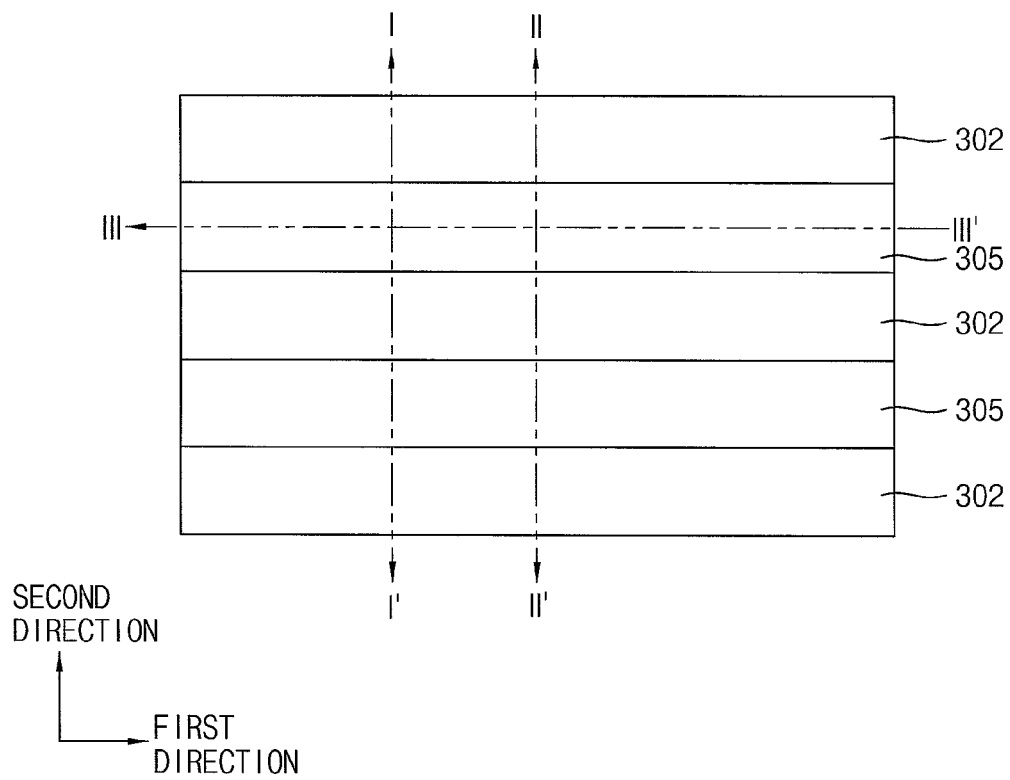
FIGS. 14 to 35 are top plan views and cross-sectional views for reference in describing a method of manufacturing a semiconductor device in accordance with example embodiments.
Figure 15:
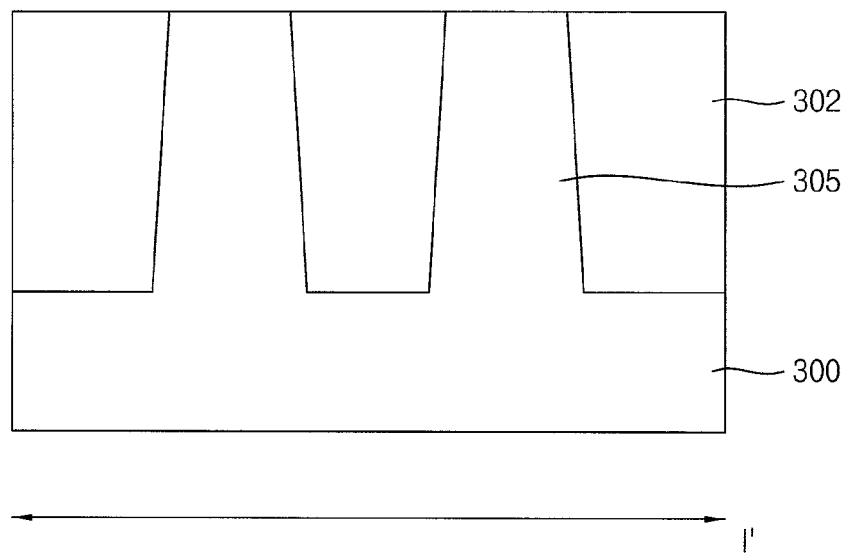
Figure 16:
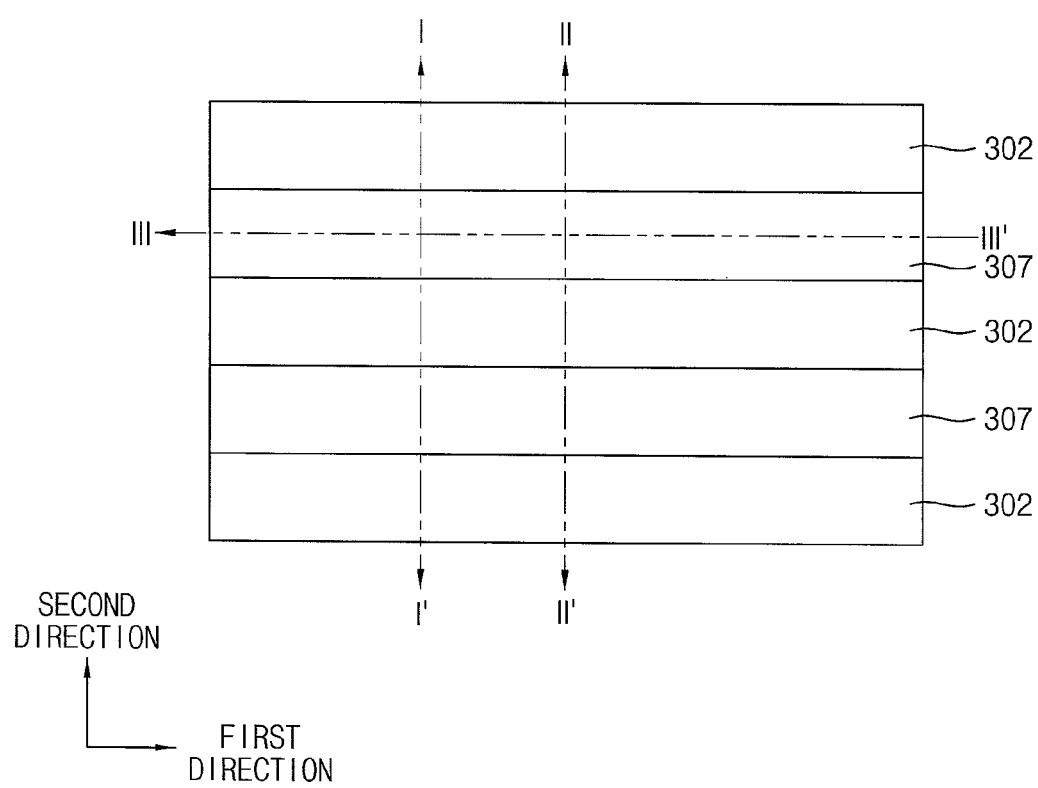
Figure 17:
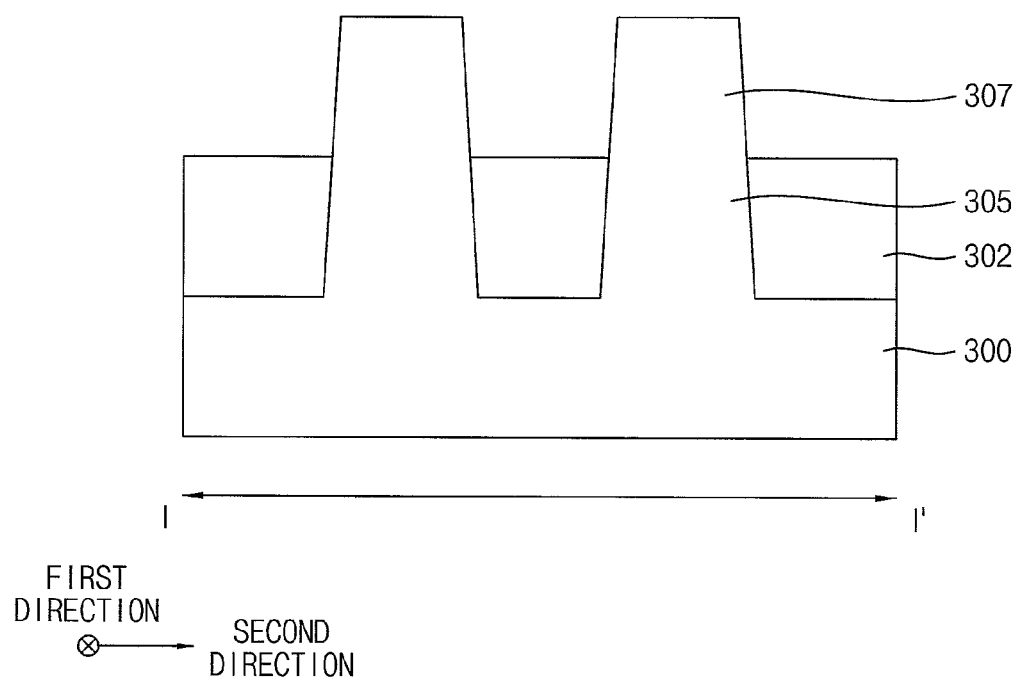
Figure 18:
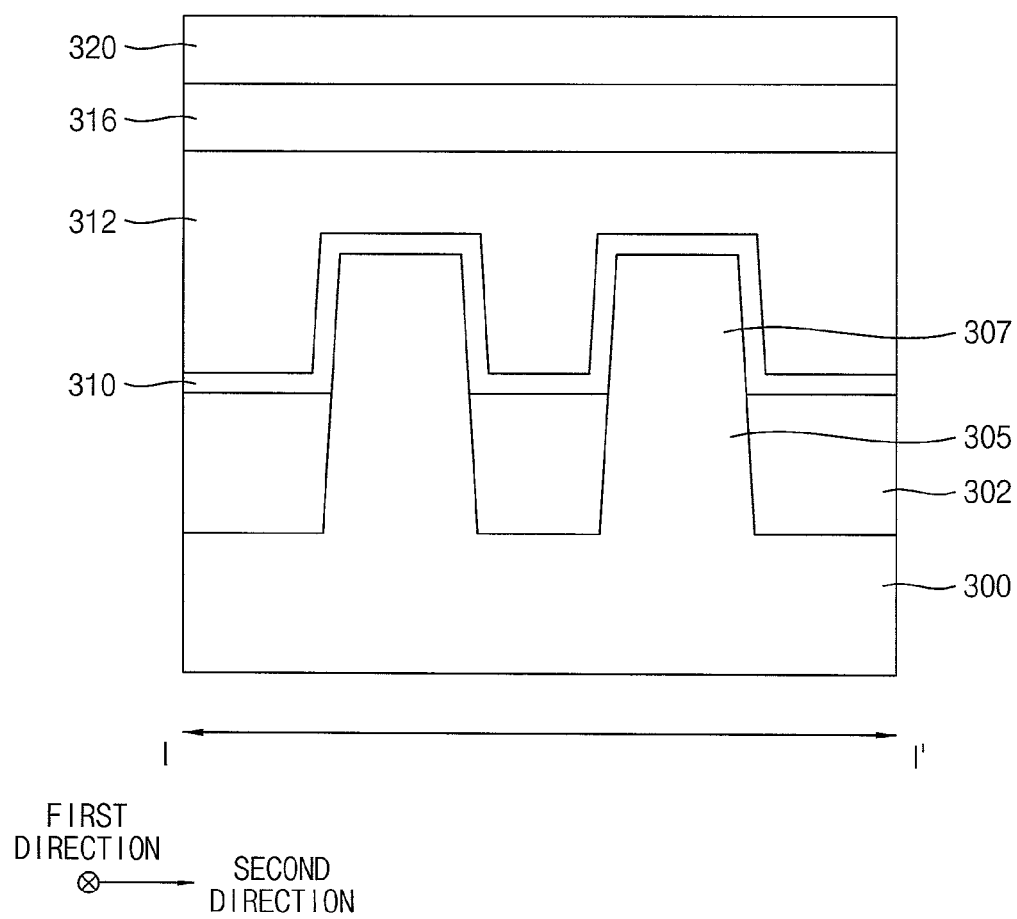
Figure 21:
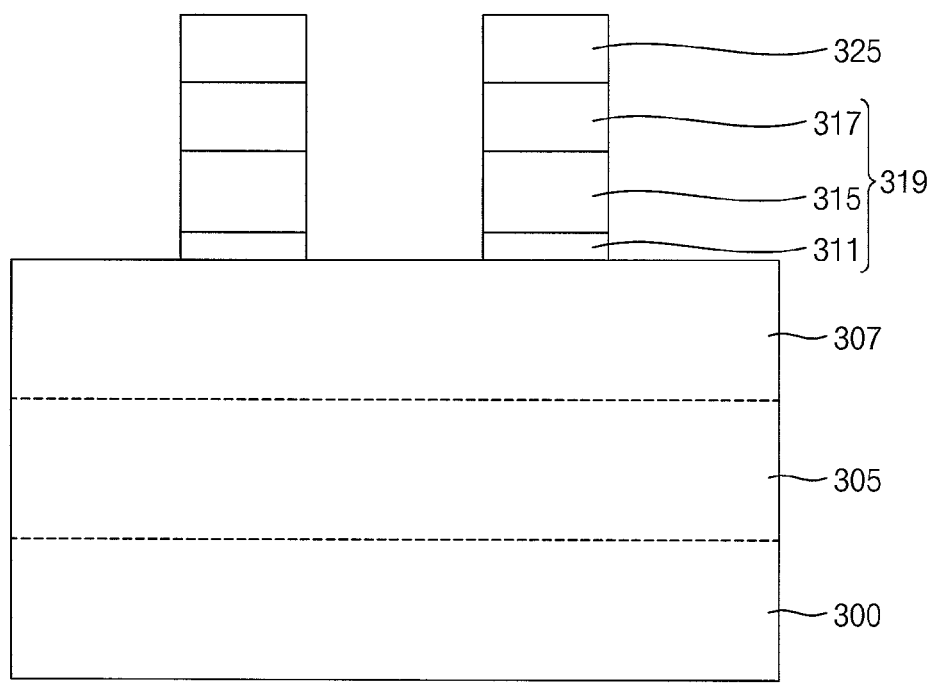
Figure 22:
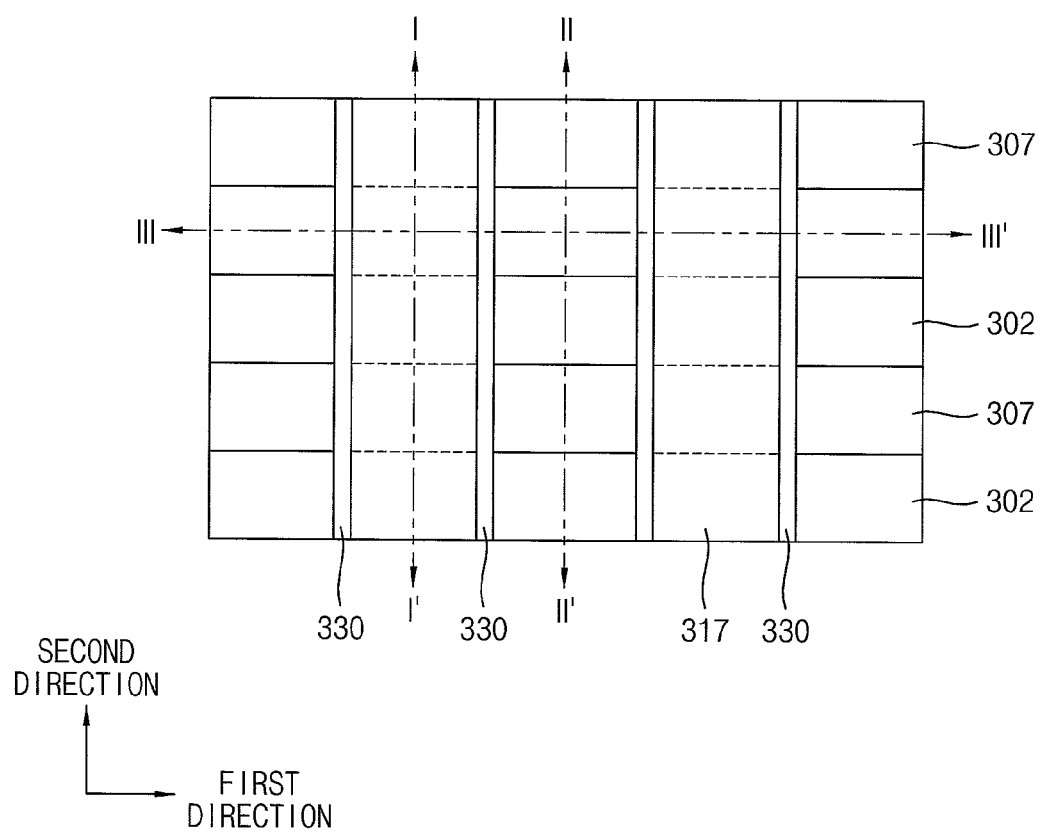

Specifically, FIGS. 14, 16 and 22 are top plan views illustrating the method. FIGS. 15, 17 and 18 are cross-sectional views taken along a line I-I' indicated in the top plan views. FIGS. 20, 24, 26 and 30 include cross-sectional views taken along lines I-I' and II-II' indicated in the top plan views. FIGS. 19, 21, 23, 25, 27 to 29, and 31 to 35 are cross-sectional views taken along a line indicated in the top plan views.

Two directions substantially parallel to a top surface of a substrate and crossing each other may be defined as a first direction and a second direction in FIGS. 14 to 35. For example, the first and second directions may be perpendicular to each other. A direction indicated by an arrow and a reverse direction thereof are considered as the same direction.

Referring to FIGS. 14 and 15, an active pattern 305 protruding from a substrate 300 may be formed.

The substrate 300 may include a semiconductor material such as Si, Ge, Si—Ge, or a group III-V compound such as InP, GaP, GaAs, GaSb, etc. In some embodiments, the substrate 300 may include an SOI substrate or a GOI substrate.

In example embodiments, the active pattern 305 is formed by a shallow trench isolation (STI) process. For example, an upper portion of the substrate 300 may be partially etched to form an isolation trench, and then an insulation layer sufficiently filling the isolation trench may be formed on the substrate 300. An upper portion of the insulation layer may be planarized by, for example, a CMP process until a top surface of the substrate 300 may be exposed to form an isolation layer 302. The insulation layer may be formed of, for example, silicon oxide.

A plurality of protrusions defined by the isolation layer 302 may be formed from the substrate 300. The protrusions may be defined as the active patterns 305. The active pattern 305 may extend linearly in the first direction, and a plurality of the active patterns 305 may be formed along the second direction.

In some embodiments, an ion-implantation process may be performed to form a well at an upper portion of the active pattern 305.

In some embodiments, the active pattern 305 may be formed from an additional channel layer. In this case, the channel layer may be formed on the substrate 300 by, for example, a selective epitaxial growth (SEG) process, and an STI process may be performed on the channel layer to form the active pattern 305.

Referring to FIGS. 16 and 17, an upper portion of the isolation layer 302 may be removed by, for example, an etch-back process so that an upper portion of the active pattern 305 may be exposed. The upper portion of the active pattern 305 exposed from a top surface of the isolation layer 302 may be defined as an active fin 307. The active fin 307 may extend in the first direction, and a plurality of the active fins 207 may be arranged along the second direction.

Figure 19:
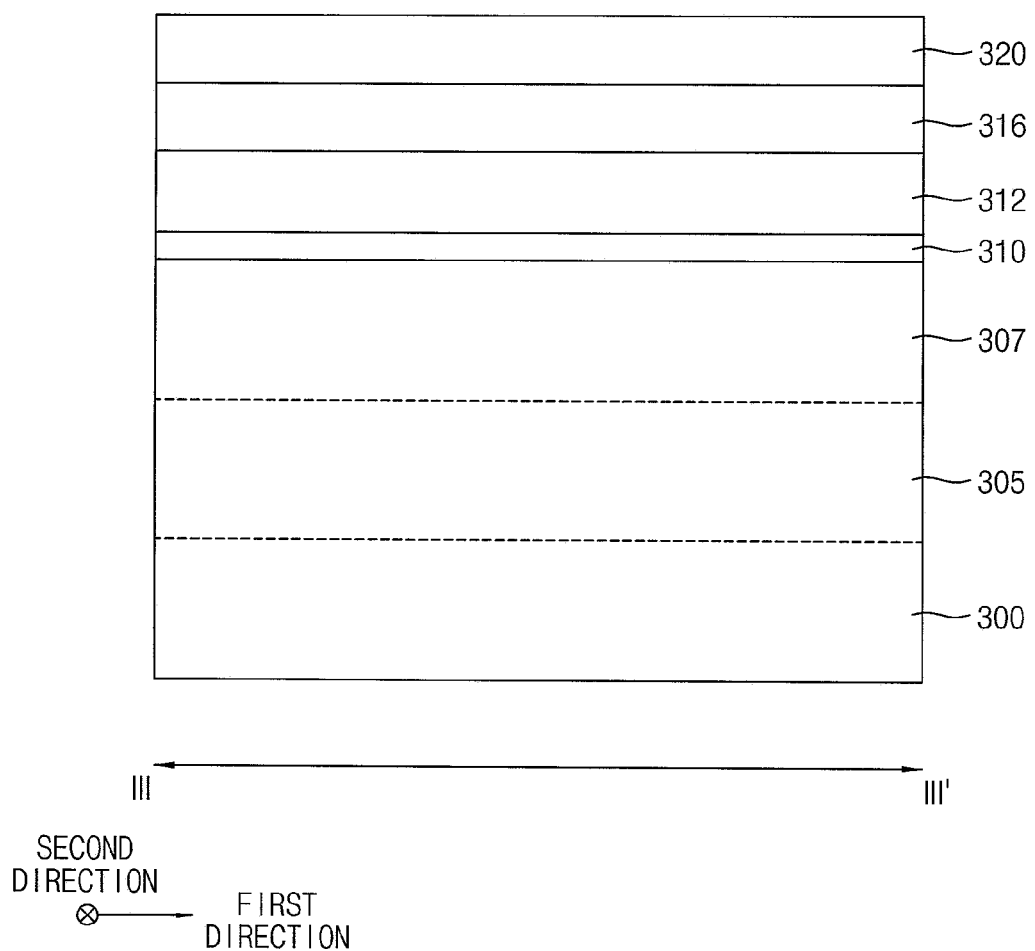

Referring to FIGS. 18 and 19, a dummy gate insulation layer 310, a dummy gate electrode layer 312 and a dummy gate mask layer 316 may be sequentially formed on the active fin 307 and the isolation layer 302. A first photoresist layer 320 may be formed on the dummy gate mask layer 316.

The dummy gate insulation layer may be formed of silicon oxide. The dummy gate electrode layer may be formed of polysilicon. The dummy gate mask layer may be formed of silicon nitride. The dummy gate insulation layer, the dummy gate electrode layer and the dummy gate mask layer may be formed by a CVD process, a sputtering process or an ALD process.

The first photoresist layer 320, as described in FIG. 2, may be formed using the photoresist composition according to example embodiments. In some embodiments, a lower coating layer is further formed before forming the first photoresist layer 320.

The photoresist composition may include the photoresist polymer, the photo-fluorine generator and the solvent. In some example embodiments, the photoresist composition further includes the sensitizer.

The photo-fluorine generator may include the sulfonium fluoride as represented by, for example, the Chemical Formula 1 above. The photoresist polymer may include the repeating unit that may include the silicon-containing leaving group. The repeating unit may be represented by, for example, the Chemical Formula 2 or Chemical Formula 3 above. The silicon-containing leaving group may be combined to a back-bone chain of the photoresist polymer via at least two linker groups as represented by the Chemical Formula 4 above.

The sensitizer, as represented by the Chemical Formulae 5 and 6 above, may include an aromatic compound including a fluorine substituent and a substituent containing an unshared electron pair. In some example embodiments, the sensitizer is coupled to the photoresist polymer as a sensitizer repeating unit as represented by the Chemical Formula 7 above.

A preliminary photoresist layer may be formed by coating the photoresist composition, and then a thermal curing process, for example, a soft-baking process may be performed thereon to form the first photoresist layer 320.

Figure 20:
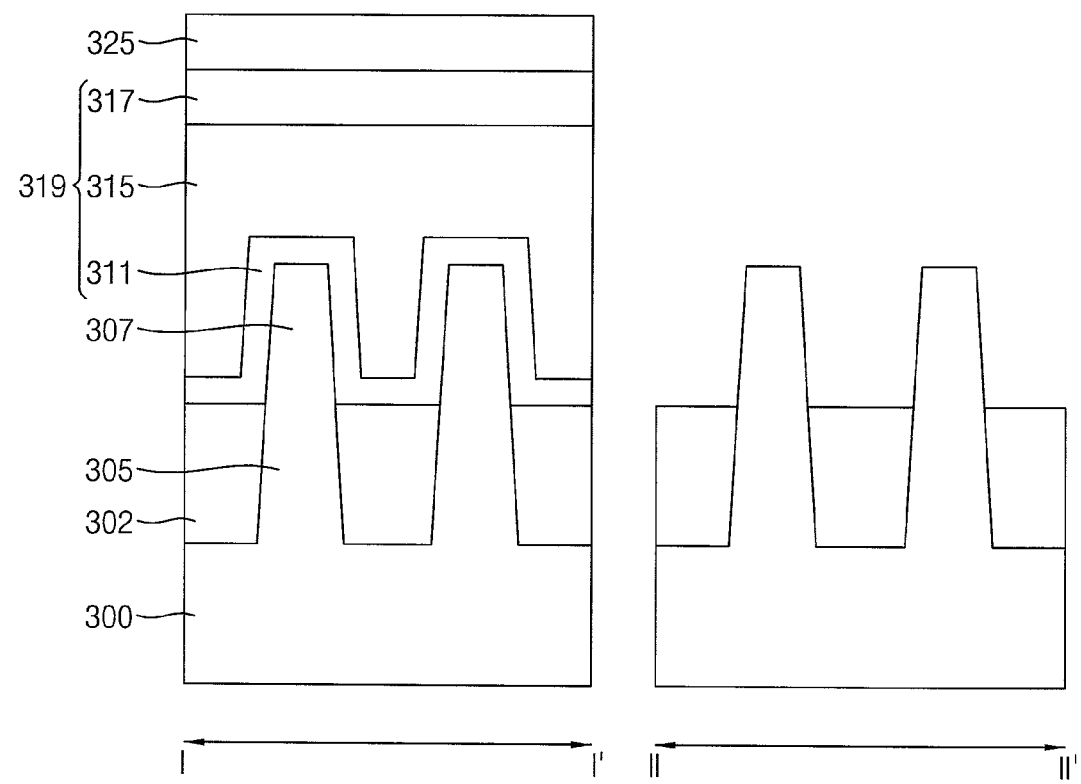

Referring to FIGS. 20 and 21, a dummy gate structure 319 may be formed by a photo-lithography process using the first photoresist layer 320.

In example embodiments, processes that are substantially the same as or similar to those previously described with reference to FIGS. 3 and 4 are performed to form a first photoresist pattern 325.

For example, an exposure process using, for example, an EUV light source may be performed to generate an active fluorine such as a fluorine ion from the photo-fluorine generator included in an exposed portion. The fluorine ion may be transferred to the silicon-containing leaving group. Accordingly, a photo-chemical reaction may be induced by, for example, the above Reaction Scheme, so that a hydrophilicity and/or a polarity of the exposed portion may be significantly increased relative to a non-exposed portion. Additionally, sensitivity in the exposed portion may be further enhanced by the sensitizer or the sensitizer repeating unit capable of releasing fluorine ions.

The exposed portion may be selectively removed by a developing process or a dry etching process to form the first photoresist pattern 325.

The dummy gate mask layer 316, the dummy gate electrode layer 312 and the dummy gate insulation layer 310 may be sequentially etched using the first photoresist pattern 325 as an etching mask. After the etching process, a dummy gate structure 319 including a dummy gate insulation pattern 311, a dummy gate electrode 315 and a dummy gate mask 317 sequentially stacked from the active fin 307 and the isolation layer 302 may be formed.

The dummy gate structure 319 may extend in the second direction, and may cross a plurality of the active fins 307. A plurality of the dummy gate structures 319 may be formed along the first direction.

The first photoresist pattern 325 may be removed by an ashing process and/or a strip process after forming the dummy gate structure 319.

Figure 23:
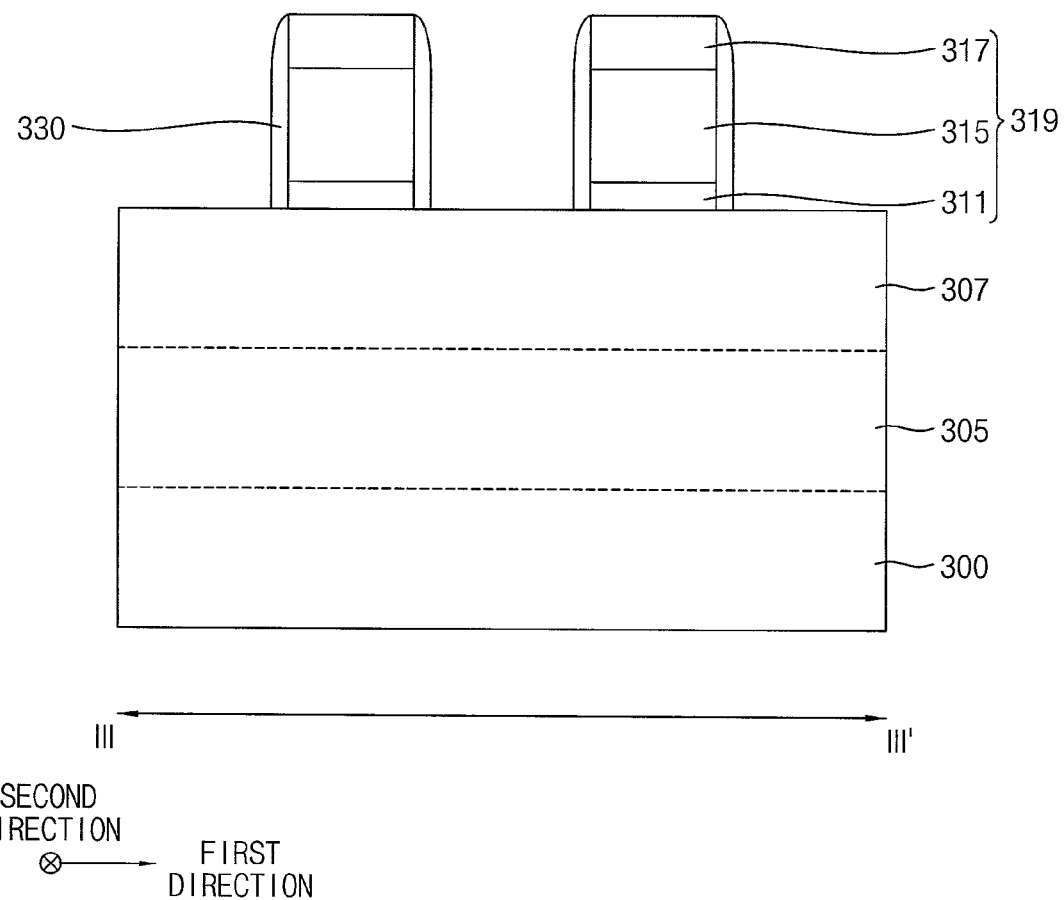

Referring to FIGS. 22 and 23, a gate spacer 330 may be formed on a sidewall of the dummy gate structure 319.

In example embodiments, a spacer layer is formed on the dummy gate structure 319, the active fin 307 and the isolation layer 302, and the spacer layer may be anisotropically etched to form the gate spacer 330. The spacer layer may be formed of a nitride, for example, silicon nitride, silicon oxynitride, silicon carbonitride, and so on.

As illustrated in FIG. 22, the gate spacer 330 may extend in the second direction together with the dummy gate structure 319.

Figure 24:
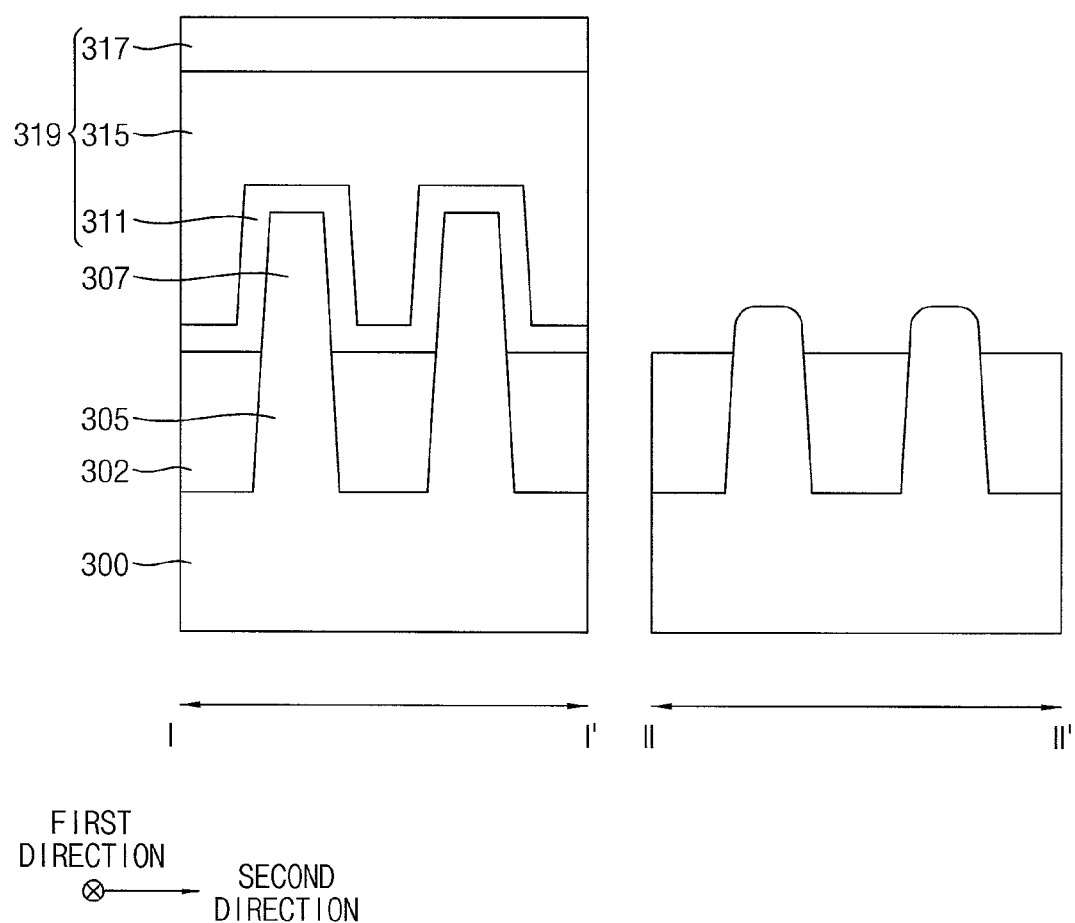
Figure 25:
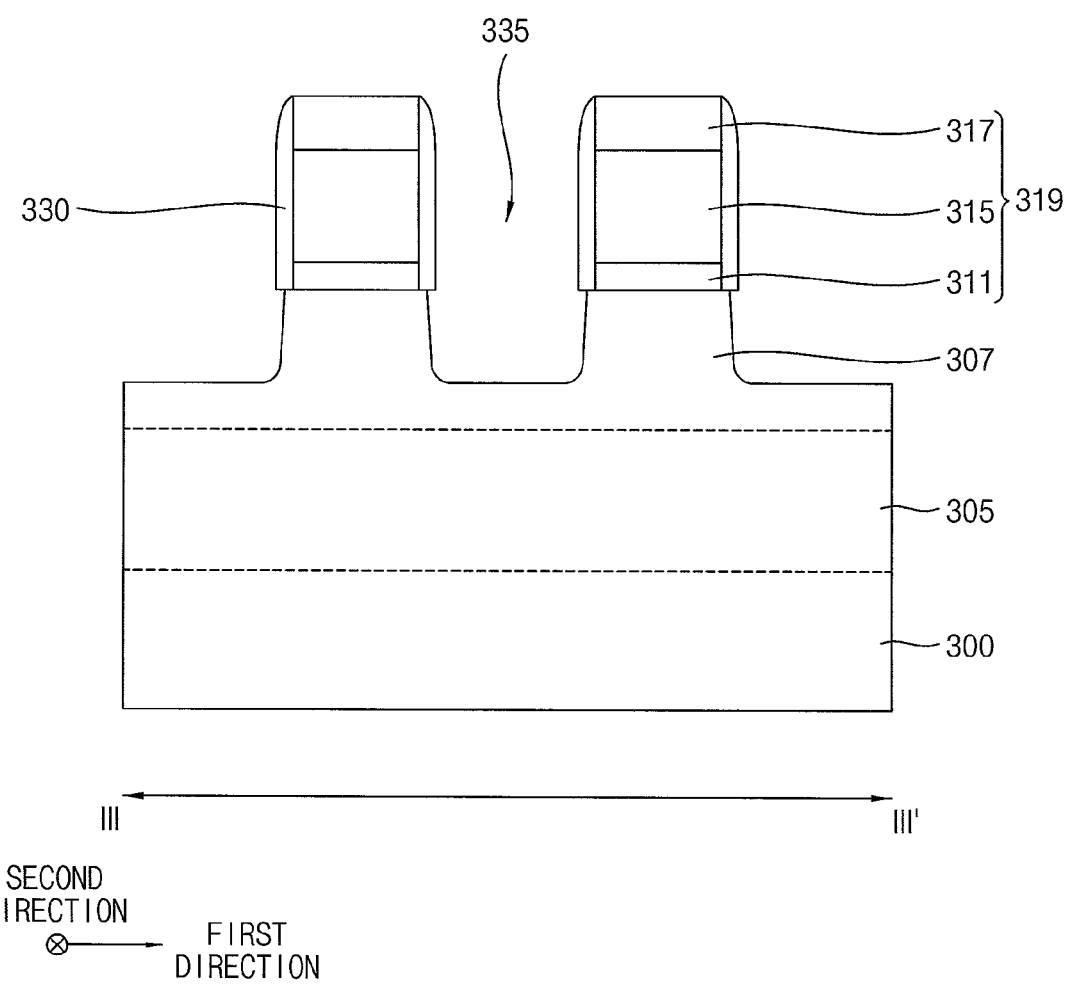

Referring to FIGS. 24 and 25, an upper portion of the active fin 307 adjacent to the gate spacer 330 and/or the dummy gate structure 319 may be etched to form a recess 335.

In the etching process for the formation of the recess 335, the gate spacer 330 may substantially serve as an etching mask. In example embodiments, an inner wall of the recess 335 have a substantially "U"-shaped profile as illustrated in FIG. 25.

In some embodiments, the recess 335 may extend to a portion of the active pattern 305 below the top surface of the isolation layer 302.

Figure 26:
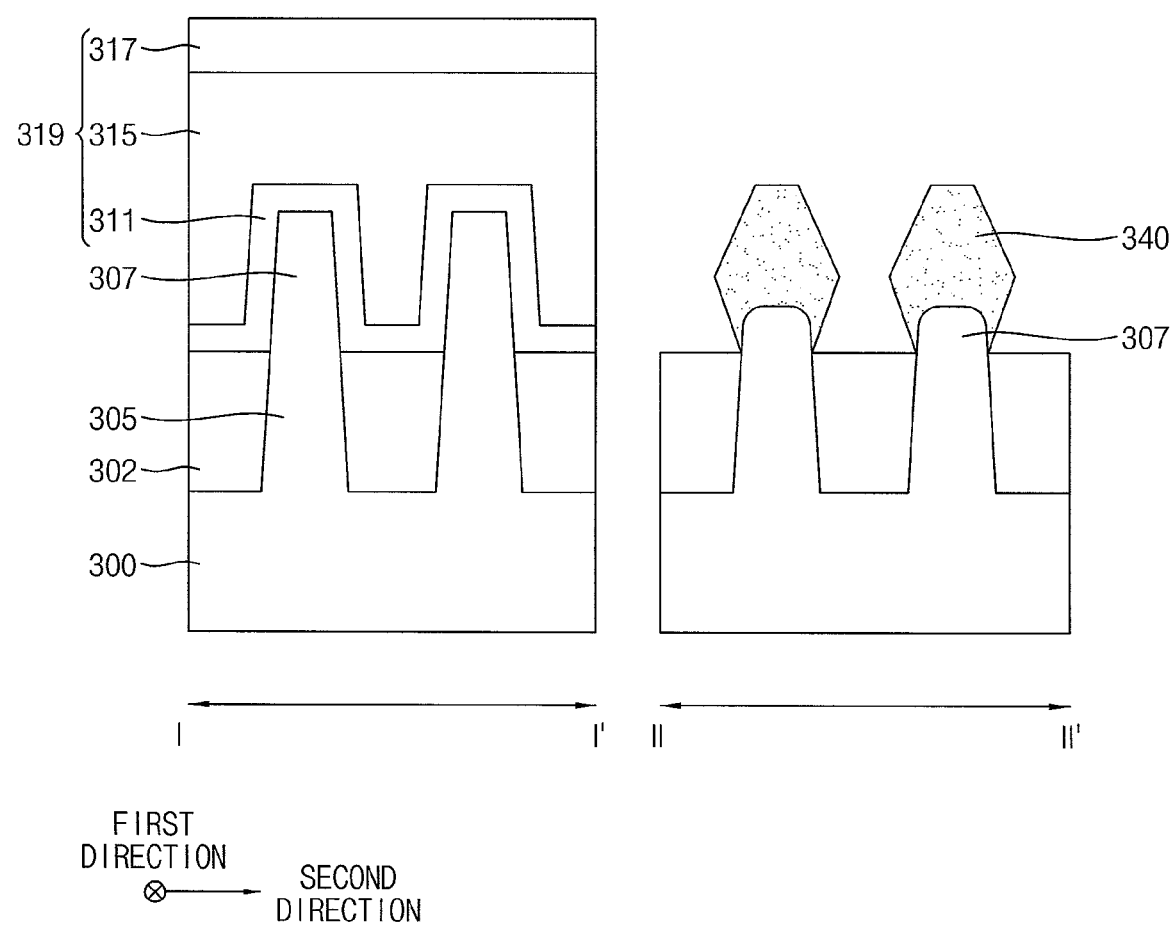
Figure 27:
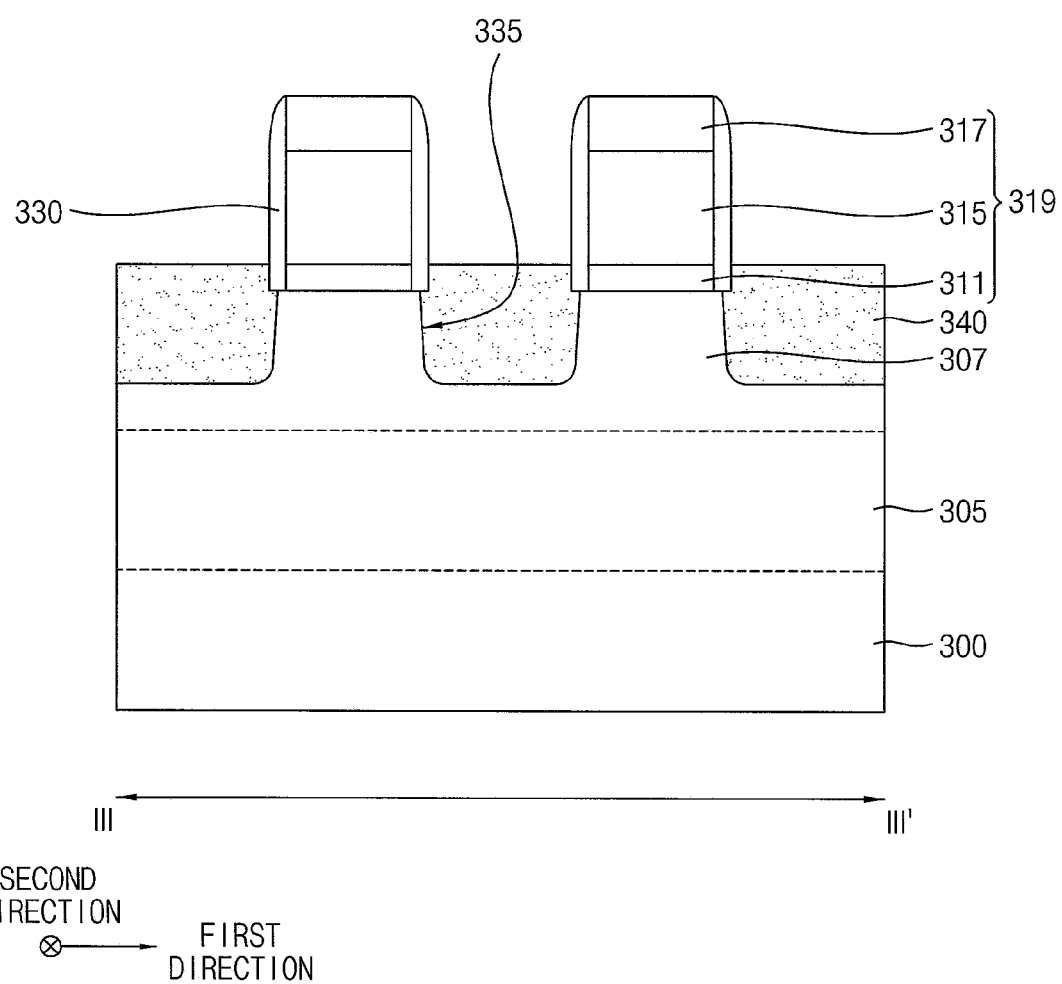

Referring to FIGS. 26 and 27, a source/drain layer 340 filling the recess 335 may be formed.

In example embodiments, the source/drain layer 340 is formed by an SEG process using the top surface of the active fin 307 exposed by the recess 335 as a seed.

In some embodiments, an n-type impurity source such as phosphine ($PH_3$) or a p-type impurity source such as diborane ($B_2H_6$) may be provided together with a silicon source such as silane in the SEG process.

The source/drain layer 340 may be grown vertically and laterally to have, for example, a polygonal cross-section as illustrated in FIG. 26. In some embodiments, the source/drain layer 340 may sufficiently fill the recess 335 to contact a lower portion of the gate spacer 330.

Figure 28:
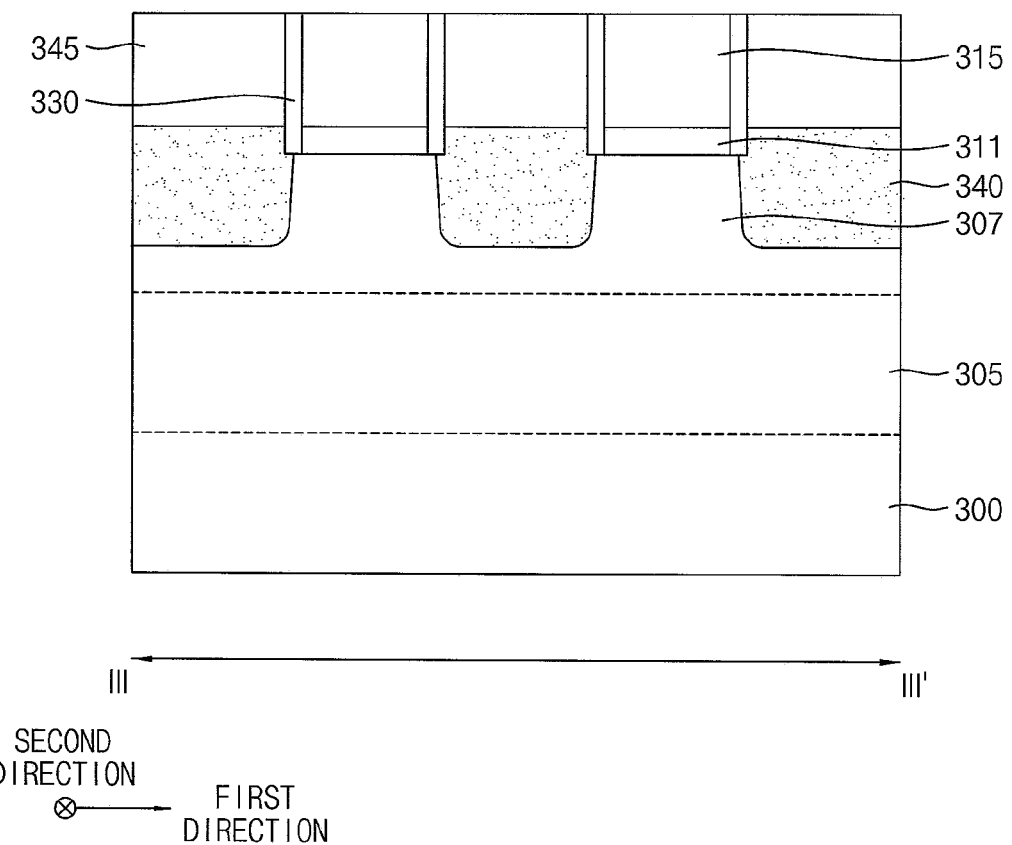

Referring to FIG. 28, a lower insulation layer 345 covering the dummy gate structure 319, the gate spacer 330 and the source/drain layers 340 may be formed on the active fin 307 and the isolation layer 302. An upper portion of the lower insulation layer 345 may be planarized by a CMP process and/or an etch-back process until a top surface of the dummy gate electrode 315 may be exposed.

In some embodiments, the dummy gate mask 317 may be removed by the CMP process, and an upper portion of the gate spacer 330 may be also partially removed.

The lower insulation layer 345 may be formed of, for example, a silicon oxide-based material by a CVD process.

Figure 29:
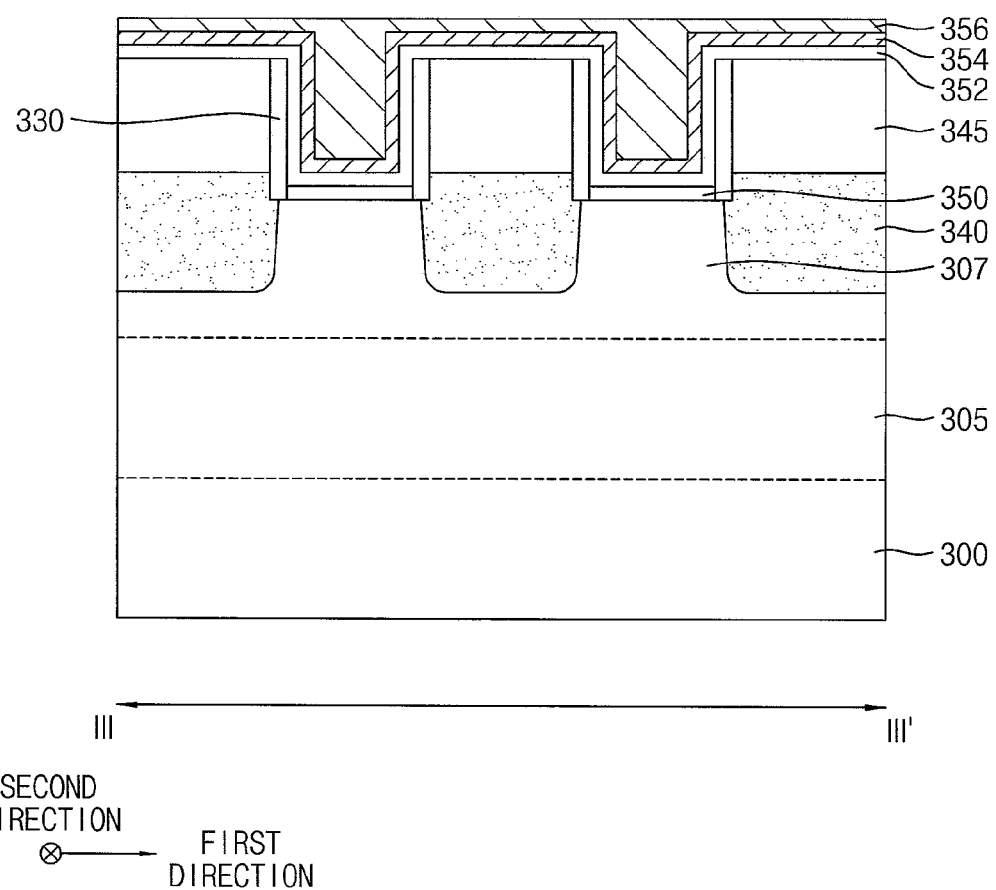

Referring to FIG. 29, the dummy gate electrode 315 and the dummy gate insulation pattern 311 may be removed. Accordingly, a trench (not illustrated) exposing an upper portion of the active fin 307 may be formed between a pair of the gate spacers 330.

The exposed active fin 307 may be thermally oxidized to form an interface layer 350. A gate insulation layer 352 may be formed along a top surface of the lower insulation layer 345, an inner wall of the trench, and top surfaces of the interface layer 350 and the isolation layer 302, and a buffer layer 354 may be formed on the gate insulation layer 352. A gate electrode layer 356 filling a remaining portion of the trench may be formed on the buffer layer 354.

The gate insulation layer 352 may be formed of a metal oxide having a high dielectric constant (high-k) such as hafnium oxide, tantalum oxide and/or zirconium oxide. The buffer layer 354 may be included for adjusting a work function of a gate electrode. The buffer layer 354 may be formed of a metal nitride such as titanium nitride, tantalum nitride and/or aluminum nitride. The gate electrode layer 356 may be formed of a metal having a low electric resistance such as aluminum, copper, tungsten, or the like.

The gate insulation layer 352, the buffer layer 354 and the gate electrode layer 356 may be formed by a CVD process, an ALD process, a PVD process, etc. In some embodiments, the interface layer 350 may be also formed by a deposition process such as a CVD process or an ALD process. In this case, the interface layer 350 may have a profile substantially the same as or similar to that of the gate insulation layer 352.

Figure 30:
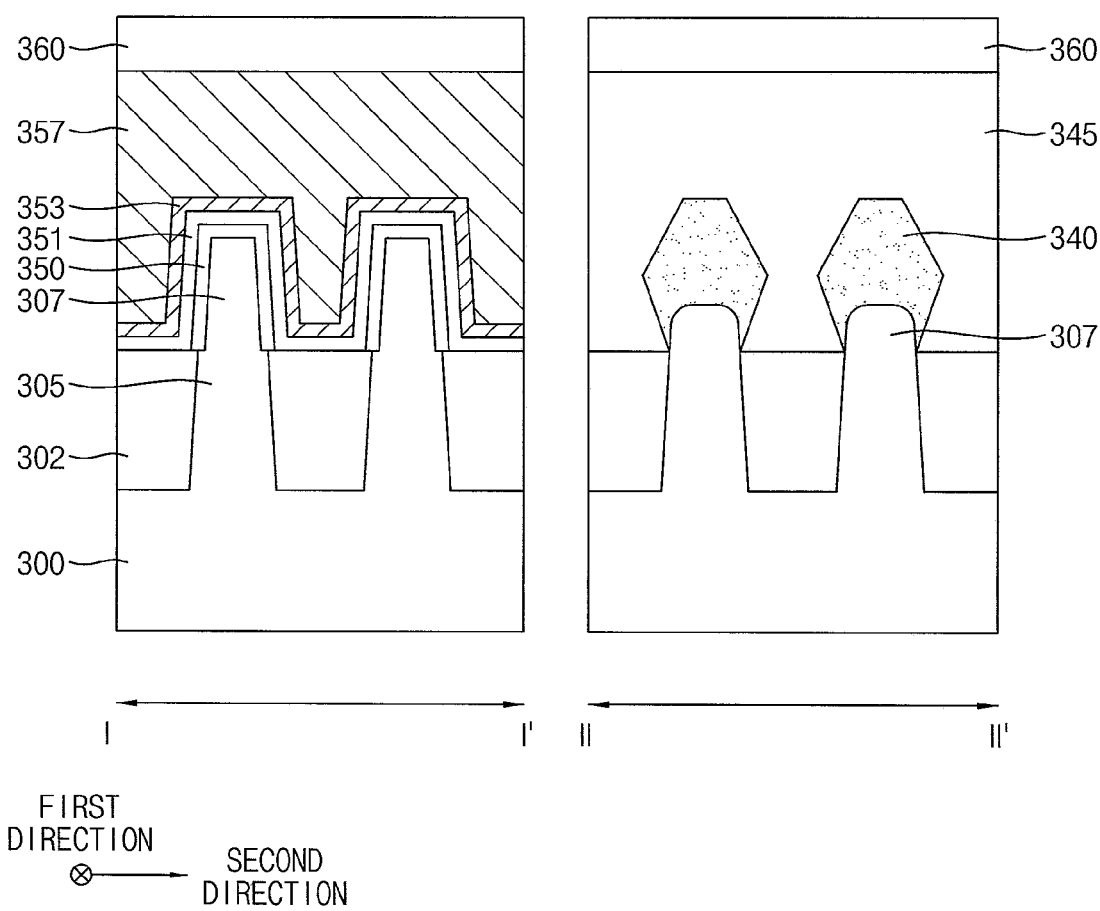
Figure 31:
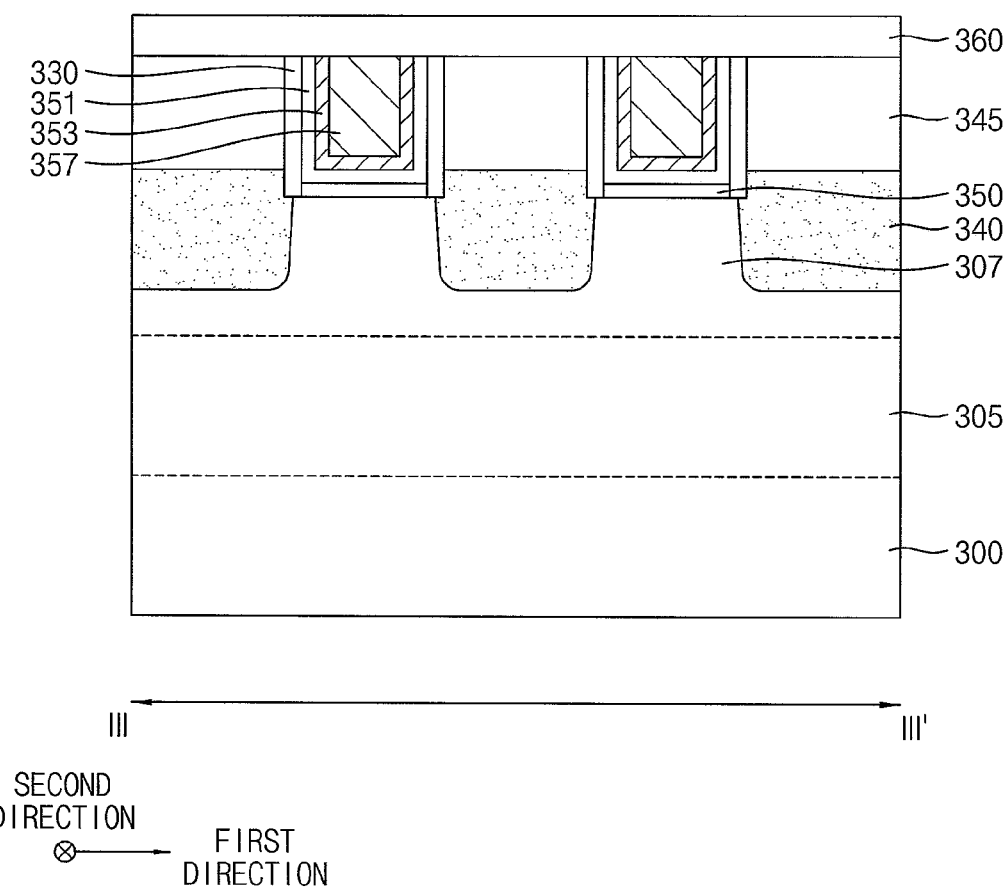

Referring to FIGS. 30 and 31, upper portions of the gate electrode layer 356, the buffer layer 354 and the gate insulation layer 352 may be planarized by, for example, a CMP process until the top surface of the lower insulation layer 345 may be exposed.

After the planarization process, a gate structure including the interface layer 350, a gate insulation pattern 351, a buffer pattern 353 and a gate electrode 357 may be defined in the trench. An NMOS transistor or a PMOS transistor having a FinFET structure may be defined by the gate structure and the source/drain layer 340.

A passivation layer 360 may be formed on the lower insulation layer 345, the gate spacers 330 and the gate structure. The passivation layer 360 may be formed of a nitride-based material such as silicon nitride or silicon oxynitride by a CVD process. A portion of the passivation layer 360 covering the gate structure may serve as a gate mask.

Figure 32:
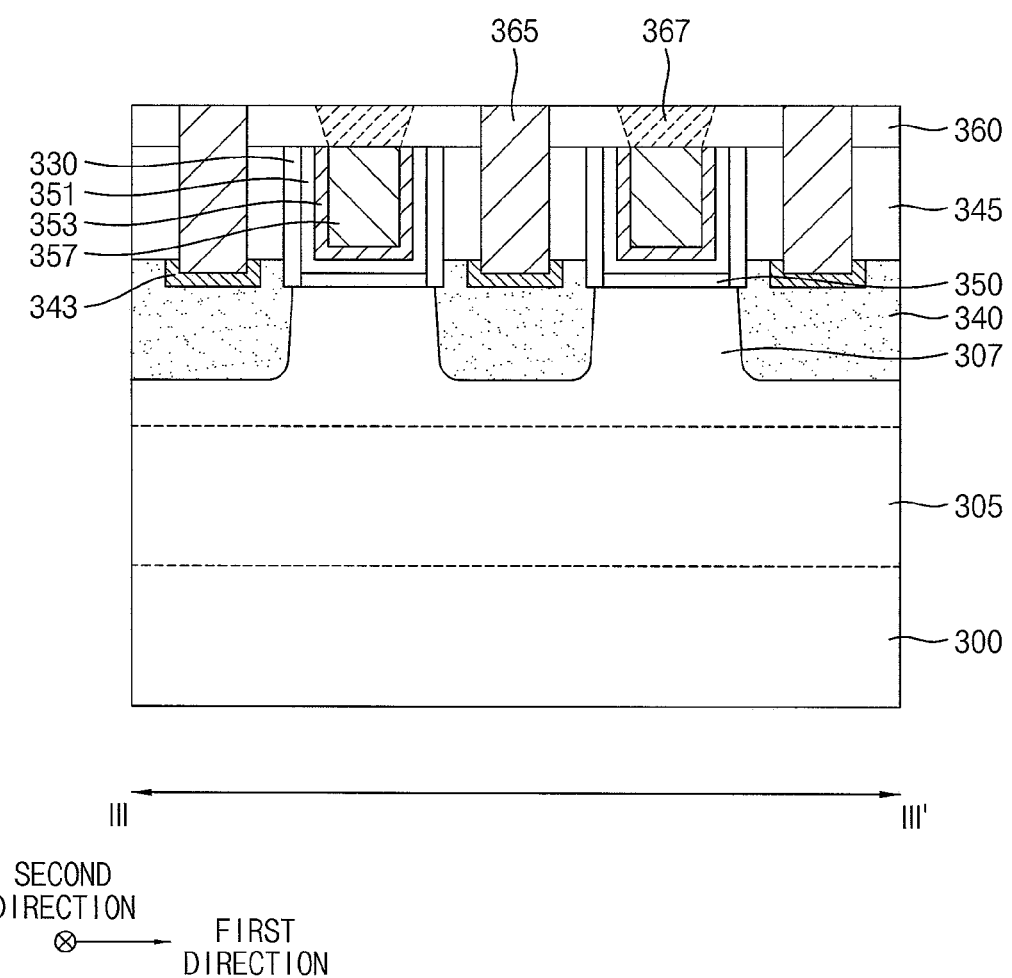

Referring to FIG. 32, an active contact 365 electrically connected to the source/drain layer 340 may be formed.

In example embodiments, the passivation layer 360 and the lower insulation layer 345 are partially etched to form a first contact hole through which the source/drain layer 340 may be exposed.

In some embodiments, while performing the etching process for forming the first contact hole, an upper portion of the source/drain layer 340 is partially removed.

In example embodiments, a silicide pattern 343 is formed at the upper portion of the source/drain layer 340 exposed through the first contact hole. For example, a metal layer may be formed on the source/drain layer 340 exposed through the first contact hole, and then a thermal treatment such as an annealing process may be performed thereon. A portion of the metal layer contacting the source/drain layer 340 may be transformed into a metal silicide by the thermal treatment. An unreacted portion of the metal layer may be removed to form the silicide pattern 343.

The metal layer may be formed of, for example, cobalt or nickel. The silicide pattern 343 may include, for example, cobalt silicide or nickel silicide.

In some embodiments, the silicide pattern 343 may protrude from a top surface of the source/drain layer 340 to fill a lower portion of the first contact hole.

Subsequently, an active contact 365 filling the first contact hole may be formed. For example, a conductive layer sufficiently filling the first contact holes may be formed on the passivation layer 360. An upper portion of the conductive layer may be planarized by a CMP process until a top surface of the passivation layer 360 may be exposed to form the active contacts 365. The conductive layer may be formed of a metal, a metal nitride, a metal silicide or a doped polysilicon.

In some embodiments, a gate contact 367 may be formed on the gate structure. The gate contact 367 may be formed through the passivation layer 360 to be in contact with a top surface of the gate electrode 357.

In some embodiments, the gate contact 367 and the active contact 365 may be formed by substantially the same etching process and deposition process. For example, a second contact hole exposing the top surface of the gate electrode 357 may be formed through passivation layer 360 together with the first contact hole. The conductive layer may also fill the second contact hole, and the gate contact 367 may be formed in the second contact hole by the CMP process.

Subsequently, a back-end-of-line (BEOL) process for forming a routing circuit of the logic semiconductor device may be performed.

Figure 33:
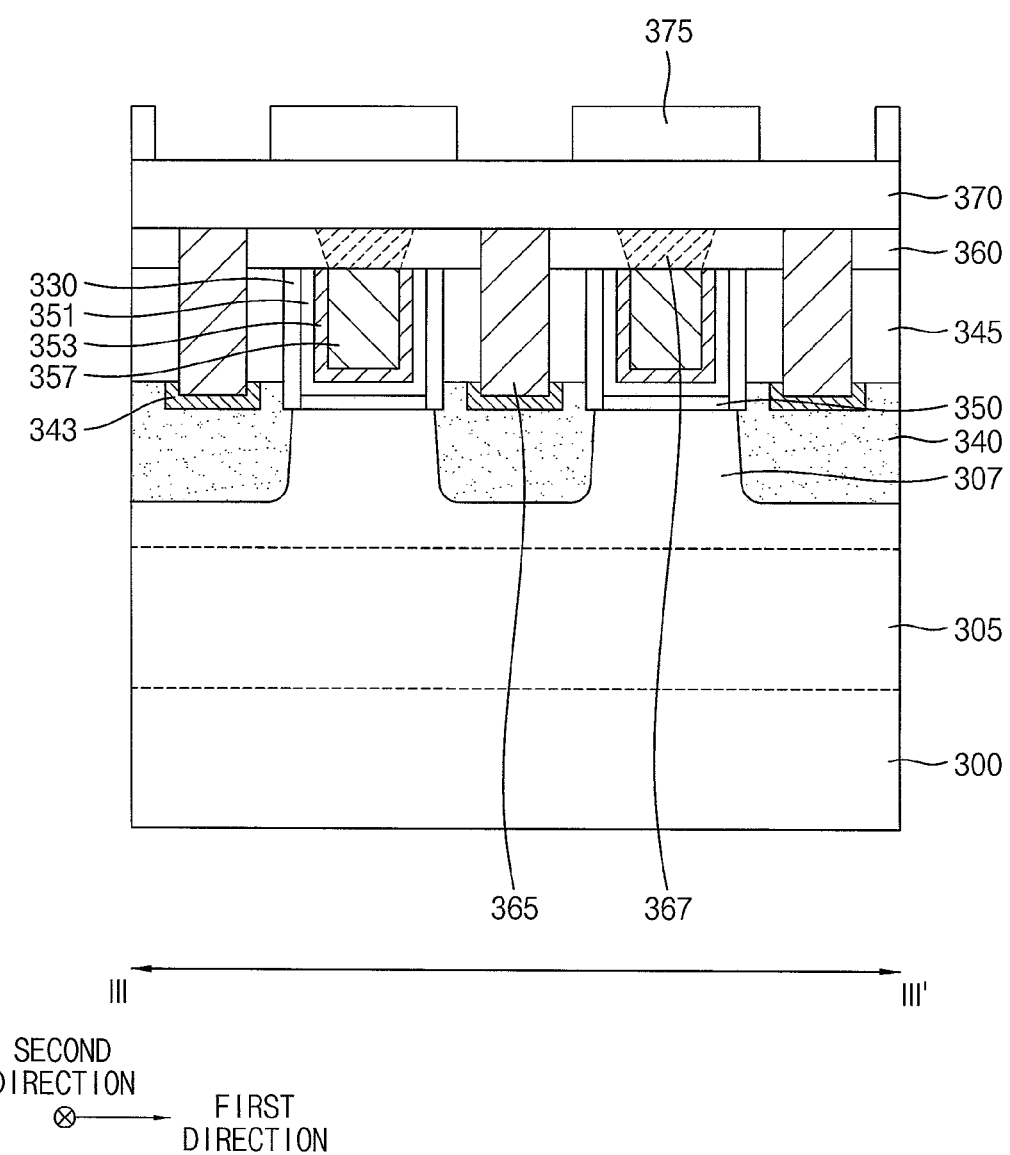

Referring to FIG. 33, a first insulating interlayer 370 may be formed on the passivation layer 360, the active contact 365 and the gate contact 367. A second photoresist pattern 375 may be formed on the first insulating interlayer 370.

In example embodiments, a second photoresist layer is formed on the first insulating interlayer 370 from a material and a process that is substantially the same as or similar to those for forming the first photoresist layer 320 previously described with reference to FIGS. 18 and 19.

The second photoresist layer may be formed using the photoresist composition according to example embodiments as described above.

Subsequently, processes that are substantially the same as or similar to those previously described with reference to FIGS. 3 and 4 may be performed to form the second photoresist pattern 375.

For example, an exposure process using, for example, an EUV light source may be performed to generate an active fluorine such as a fluorine ion from a photo-fluorine generator included in an exposed portion of the second photoresist layer. The fluorine ion may be transferred to a silicon-containing leaving group of a photoresist polymer. Accordingly, a photo-chemical reaction may be induced by, for example, the above Reaction Scheme, so that a hydrophilicity and/or a polarity of the exposed portion may be significantly increased relative to a non-exposed portion. Additionally, sensitivity in the exposed portion may be further enhanced by a sensitizer or a sensitizer repeating unit capable of releasing fluorine ions.

The exposed portion may be selectively removed by a developing process or a dry etching process to form the second photoresist pattern 375.

Figure 34:
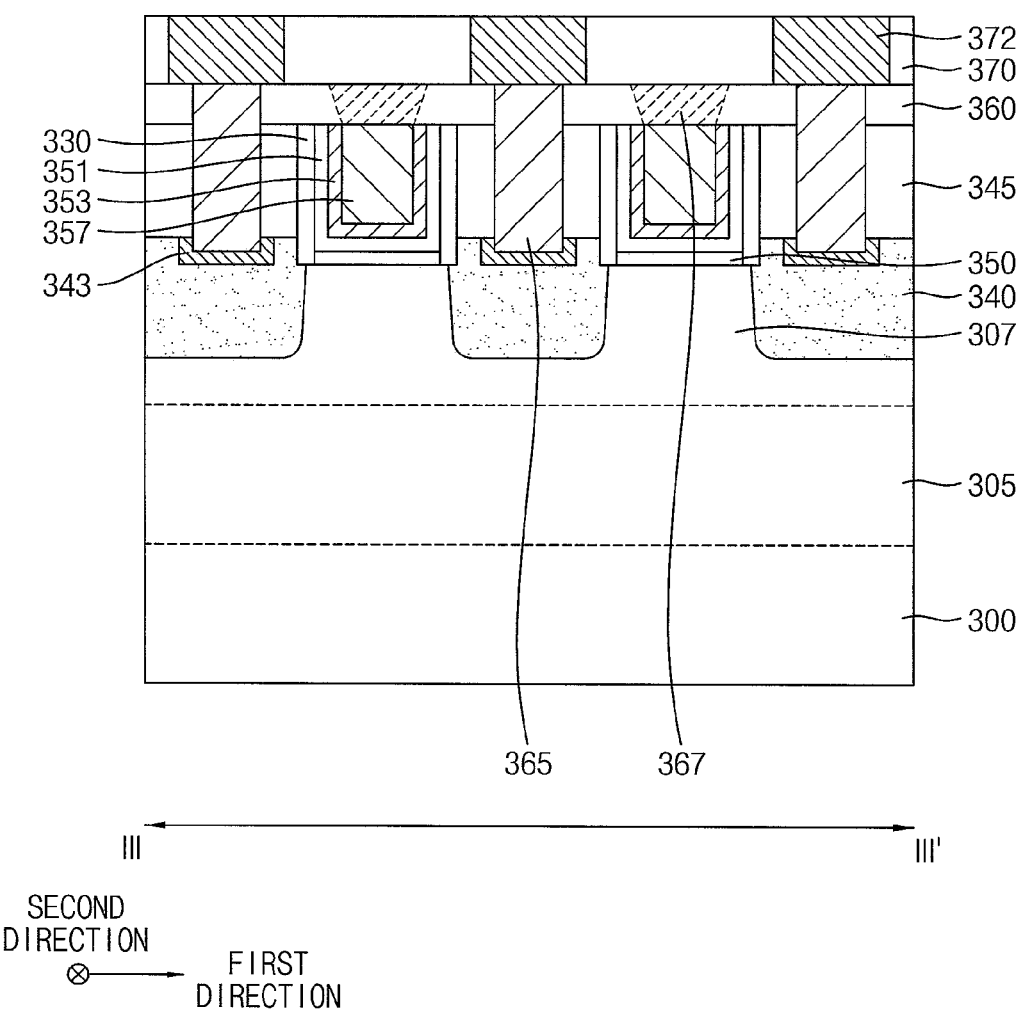

Referring to FIG. 34, the first insulating interlayer 370 may be partially removed using the second photoresist pattern 375 as an etching mask to form a first opening through which the active contact 365 may be exposed. The first opening may be filled with a conductive material to form a first wiring 372 electrically connected to the active contact 365.

Figure 35:
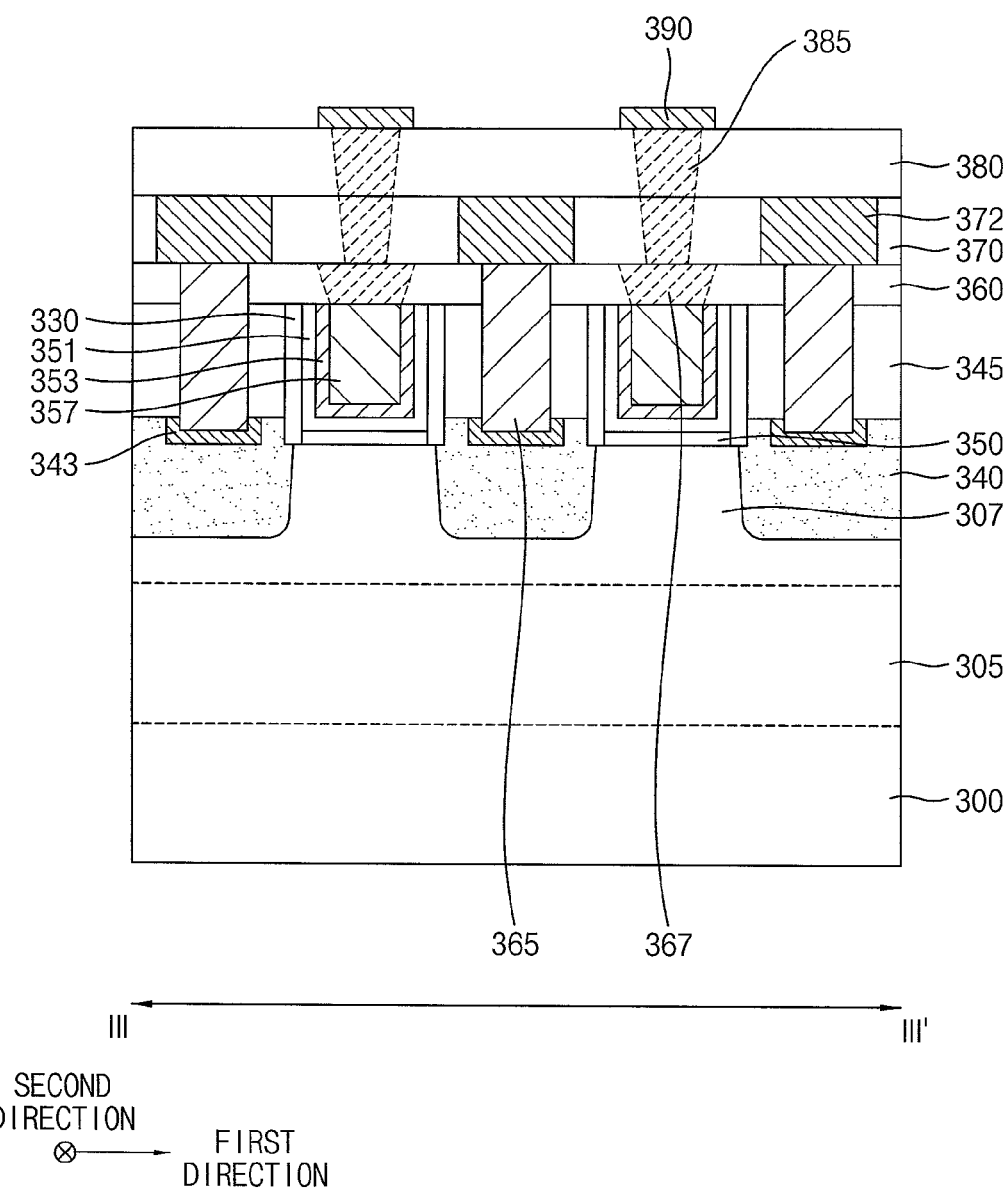

Referring to FIG. 35, a second insulating interlayer 380 covering the first wirings 372 may be formed on the first insulating interlayer 370. The first and second insulating interlayers 370 and 380 may be formed of a low-k polysiloxane or silesquioxane-based oxide by a CVD process, a spin coating process, etc.

A second opening extending through the second insulating interlayer 380 and the first insulating interlayer 370 may be formed such that a top surface of the gate contact 367 may be exposed. The second opening may be formed by processes substantially the same as or similar to those described with reference to FIGS. 33 and 34.

For example, the second opening may be formed using a photo-lithography process system with an improved sensitivity based on a photo-fluorine generator according to example embodiments as described above.

A through contact 385 electrically connected to the gate contact 367 may be formed by filling the second opening with a conductive material.

A metal layer may be formed on the second insulating interlayer 380 to cover the through contact 385. The metal layer may be patterned to form a second wiring 390 electrically connected to the through contact 385.

The second wiring 390 may be also formed by the photo-lithography process system based on the photo-fluorine generator according to example embodiments.

As described above, according to example embodiments of a photoresist composition of the present inventive concepts, a photo-fluorine generator creating a fluorine ion is used instead of a photo-acid generator (PAG). However, it is noted that not all embodiments of the inventive concepts are limited to photoresist compositions devoid of PAG. That is, the photoresist compositions of some embodiments may be devoid of PAG, and the photoresist compositions of other embodiment may include PAG.

The photo-fluorine generator may include a sulfonium fluoride, and a generation of the fluorine ion may be facilitated by a sulfonium group. The fluorine ion may attack, for example, a silicon-containing leaving group contained in a photoresist polymer. Accordingly, hydrophilicity and/or polarity of an exposed portion of the photoresist polymer may be increased, and the exposed portion may be selectively removed by a developing process. Further, a repeating unit or a compound capable of photo-chemically generating a plurality of fluorine ions may be used as a sensitizer to amplify the generation of the fluorine ions. Therefore, a photo-lithography process system with a high sensitivity may be realized without an intervention of an acid.

The photoresist composition may be utilized in a photo-lithography process for forming a fine pattern having a critical dimension below, for example, about 20 nm or about 10 nm. Wirings, contacts, insulation patterns, and so on, having fine dimensions of various semiconductor devices may be formed using the photo-lithography process.

The foregoing is illustrative of example embodiments and is not to be construed as limiting thereof. Although a few example embodiments have been described, those skilled in the art will readily appreciate that many modifications are possible in the example embodiments without materially departing from the novel teachings and advantages of the present inventive concept. Accordingly, all such modifications are intended to be included within the scope of the present inventive concept as defined in the claims. In the claims, means-plus-function clauses are intended to cover the structures described herein as performing the recited function and not only structural equivalents but also equivalent structures. Therefore, it is to be understood that the foregoing is illustrative of various example embodiments and is not to be construed as limited to the specific example embodiments disclosed, and that modifications to the disclosed example embodiments, as well as other example embodiments, are intended to be included within the scope of the appended claims.

What is claimed is:

1. A method of manufacturing a patterned device, comprising:
    forming an object layer on a substrate;
    forming a photoresist layer on the object layer by coating the object layer with a photoresist composition, the photoresist composition comprising a photoresist polymer including a repeating unit to which a silicon-containing leaving group is combined, a photo-fluorine generator including a sulfonium fluoride, and a solvent;
    performing an exposure process on the photoresist layer such that the photoresist layer includes an exposed portion and a non-exposed portion;
    removing the exposed portion to form a photoresist pattern; and
    patterning the object layer using the photoresist pattern as a mask,
    wherein the silicon-containing leaving group is connected to a back-bone chain of the photoresist polymer via at last two linker groups.

2. The method of claim 1, wherein performing the exposure process includes separating the silicon-containing leaving group from the photoresist polymer by a fluorine ion created from the photo-fluorine generator in the exposed portion.

3. The method of claim 2, wherein a hydroxyl group or a carboxylic group is created at a site from which the silicon-containing leaving group of the exposed portion is removed.

4. The method of claim 3, wherein the exposed portion is more hydrophilic or more polar than the non-exposed portion.

5. The method of claim 4, wherein removing the exposed portion includes a developing process using a hydrophilic solution.

6. The method of claim 2, wherein the photoresist composition further includes a sensitizer capable of generating fluorine, and
    wherein performing the exposure process includes separating the silicon-containing leaving group from the photoresist polymer by a fluorine ion created from the sensitizer and the fluorine ion created from the photo-fluorine generator.

7. The method of claim 6, wherein the sensitizer includes an aromatic compound that includes a fluorine substituent and a substituent including an unshared electron pair.

8. The method of claim 1, wherein performing the exposure process includes using an extreme ultraviolet (EUV) light source.

9. A method of manufacturing a semiconductor device, comprising:
    forming an isolation layer on a substrate to define active patterns of the substrate;
    forming a gate structure on the isolation layer and the active patterns;
    forming contacts electrically connected to the active patterns;
    forming an insulating interlayer covering the gate structure and the contacts;
    forming a photoresist layer on the insulating interlayer by coating the insulating layer with a photoresist composition, the photoresist composition comprising a photoresist polymer including a repeating unit to which a silicon-containing leaving group is combined, a photo-fluorine generator including a sulfonium fluoride, and a solvent;
    partially removing the photoresist layer to form a photoresist pattern;
    partially etching the insulating interlayer using the photoresist pattern as a mask to form openings through which the contacts are exposed; and
    forming wirings in the openings, the wirings being electrically connected to the contacts,
    wherein the silicon-containing leaving group is connected to a back-bone chain of the photoresist polymer via at least two linker groups.

10. The method of claim 9, wherein partially removing the photoresist layer to form the photoresist pattern includes:
    performing an exposure process on the photoresist layer such that the photoresist layer includes a non-exposed portion and an exposed portion in which the silicon-containing leaving group is removed from the photoresist polymer by a fluorine ion generated from the photo-fluorine generator; and removing the exposed portion from the photoresist layer.

11. The method of claim 10, wherein performing the exposure process includes using an extreme ultraviolet (EUV) light source.

12. The method of claim 10, wherein the photoresist composition further includes a sensitizer capable of generating fluorine.

13. The method of claim 12, wherein the exposure process further includes separating the silicon-containing leaving group from the photoresist polymer by a fluorine ion created from the sensitizer.

* * * * *